US011727674B2

(12) United States Patent
Bentaieb et al.

(10) Patent No.: US 11,727,674 B2
(45) Date of Patent: Aug. 15, 2023

(54) SYSTEMS AND METHODS FOR GENERATING HISTOLOGY IMAGE TRAINING DATASETS FOR MACHINE LEARNING MODELS

(71) Applicant: TEMPUS LABS, INC., Chicago, IL (US)

(72) Inventors: Aïcha Bentaieb, Mountain View, CA (US); Martin Christian Stumpe, Belmont, CA (US); Aly Azeem Khan, Chicago, IL (US)

(73) Assignee: TEMPUS LABS, INC., Chicago, IL (US)

( * ) Notice: Subject to any disclaimer, the term of this patent is extended or adjusted under 35 U.S.C. 154(b) by 0 days.

(21) Appl. No.: 17/549,040

(22) Filed: Dec. 13, 2021

(65) Prior Publication Data

US 2022/0189150 A1 Jun. 16, 2022

Related U.S. Application Data

(60) Provisional application No. 63/199,185, filed on Dec. 11, 2020.

(51) Int. Cl.
*G16C 20/70* (2019.01)
*G06V 20/69* (2022.01)
*G06V 10/774* (2022.01)

(52) U.S. Cl.
CPC ........ *G06V 10/7747* (2022.01); *G06V 20/698* (2022.01); *G16C 20/70* (2019.02)

(58) Field of Classification Search
None
See application file for complete search history.

(56) References Cited

U.S. PATENT DOCUMENTS

| | | |
|---|---|---|
| 2019/0347557 A1 | 11/2019 | Khan |
| 2020/0258223 A1 | 8/2020 | Yip et al. |
| 2020/0342597 A1 | 10/2020 | Chukka et al. |
| 2020/0372235 A1 | 11/2020 | Peng et al. |

FOREIGN PATENT DOCUMENTS

WO WO-2019/157078 A1 8/2019

OTHER PUBLICATIONS

Burlingame et al. (Scientific Reports: Nature Research (2020) vol. 10:14 pages; published Oct. 15, 2020).*
Chen and Srinivas (Automatic Lymphocyte Detection in H&E Images with Deep Neural Networks; ArXiv161203217 Cs; 2016:11 pages).*
Feng et al. (JCI Insight (2017) vol. 2(14):18 pages).*
Komura et al. (Computational and Structural Biotechnology Journal (2018 ) vol. 16:34-42).*
Naik et al. (Nature Communications (2020) vol. 11,5727:8 pages).*
Automated, High-Flexibility IHC/ISH Slide Staining for Assay Development, Discovery Ultra IHC/ISH Research Platform, Roche, downloaded from the Internet at: https://diagnostics_roche.com/us/en/products/instruments/discovery-ultra-research.html (Accessed date: Jan. 6, 2022), 4 pages.
Blank et al., The "cancer immunogram", Science, 352(6286):658-60 (2016).
Bulten et al., Epithelium segmentation using deep learning in H&E-stained prostate specimens with immunohistochemistry as reference standard, Sci. Rep., 9:864 (2019), 10 pages.
Chuah et al., High-dimensional immuno-profiling in cancer: implications for immunotherapy, Journal for ImmunoTherapy of Cancer, 8:e000363 (2020), 10 pages.
Jackson et al., A machine learning algorithm for simulating immunohistochemistry: development of SOX10 virtual IHC and evaluation on primarily melanocytic neoplasms, Modern Pathology, 33:1638-48 (2020).
Lu et al., Comparison of biomarker modalities for predicting response to PD-1/PD-L1 checkpoint blockade: A systematic review and meta-analysis, JAMA Oncology, 5(8):1195-204 (2019).
Morrison et al., Brightfield multiplex immunohistochemistry with multispectral imaging, Laboratory Investigation, 100:1124-36 (2020).
Naberhuis, Overview of Multiplex Immunohistochemistry, downloaded from the Internet at: <https://www.biomol.com/resources/biomol-blog/overview-of-multiplex-immunohistochemistry> (2020), 5 pages.
Nadarajan et al., Automated multi-class ground-truth labeling of H&E images for deep learning using multiplexed fluorescence microscopy, Proceedings vol. 10956, Medical Imaging 2019: Digital Pathology; 109560J (2019), 11 pages.
Parra et al., Validation of multiplex immunofluorescence panels using multispectral microscopy for immune-profiling of formalin-fixed and paraffin-embedded human tumor issues, Sci. Rep., 7:13380 (2017), 11 pages.
Puccini et al., Overcoming resistance to anti-PD1 and anti-PD-L1 treatment in gastrointestinal malignancies, Journal of Immunotherapy of Cancer, 8:000404 (2020), 15 pages.

(Continued)

*Primary Examiner* — Lori A. Clow
(74) *Attorney, Agent, or Firm* — Marshall, Gerstein & Borun LLP

(57) ABSTRACT

A system and method are provided for training and using a machine learning model to analyze hematoxylin and eosin (H&E) slide images, where the machine learning model is trained using a training data set comprising a plurality of unmarked H&E images and a plurality of marked H&E images, each marked H&E image being associated with one unmarked H&E image and each marked H&E image including a location of one or more molecules determined by analyzing a multiplex IHC image having at least two IHC stains, each IHC stain having a unique color and a unique target molecule. Predicted molecules and locations identified with the machine learning model result in an immunotherapy response class being assigned to the H&E slide image.

30 Claims, 15 Drawing Sheets

(3 of 15 Drawing Sheet(s) Filed in Color)

(56) References Cited

OTHER PUBLICATIONS

Taube et al., The Society for Immunotherapy of Cancer statement on best practices for multiplex immunohistochemistry (IHC) and immunofluorescence (IF) staining and validation, Journal for ImmunoTherapy of Cancer, 8:e000155 (2020).
What is Immunoscore®? Veracyte, South San Francisco, California, Downloaded from the Internet at:https://io.veracyte.com/what-is-immunoscore/ (Accessed date: Jan. 6, 2022) 5 pages.
Bentaieb et al., Adversarial stain transfer for histopathology image analysis, IEEE Transactions on Medical Imaging, 37(3): 792-802 (Mar. 2018).
International Application No. PCT/US2021/063068, International Search Report and Written Opinion, dated Apr. 27, 2022.

\* cited by examiner

FCN Tile-Resolution Classifier

| Layer Name | Output Size | Sub Layer |
|---|---|---|
| Input Layer | (434+32N)×(434+32N)×3 | |
| Conv1 | (214+16N)×(214+16N)×64 | |
| Max Pool | (106+8N)×(106+8N)×64 | |
| Conv2_x | (98+8N)×(98+8N)×64 | Four 3×3 Conv Layers |
| Conv3_x | (42+4N)×(42+4N)×128 | Four 3×3 Conv Layers |
| Conv4_x | (14+2N)×(14+2N)×256 | Four 3×3 Conv Layers |
| Conv5_x | N×N×512 | Four 3×3 Conv Layers |
| Concat | N×N×(512+64+64) | |
| 1×1 Conv | N×N #Classes | |
| Softmax | N×N | |

No Padding

FIG. 6B

Filter W1 (3×3×3)
W1[:, :, 0]

| 0 | 0 | 1 |
|---|---|---|
| 1 | 1 | 0 |
| 0 | 0 | 0 |

W0[:, :, 1]

| 1 | 0 | 0 |
|---|---|---|
| 1 | -1 | 1 |
| -1 | 0 | 0 |

W0[:, :, 2]

| -1 | 1 | 0 |
|---|---|---|
| 0 | -1 | 1 |
| 1 | 0 | -1 |

Bias B1 (1×1×1)
B1[:, :, 0]

| 0 |
|---|

Output Volume (3×3×2)
O[:, :, 0]

| -6 | -7 | -5 |
|---|---|---|
| -9 | -6 | -9 |
| 3 | -5 | -8 |

O[:, :, 1]

| 2 | 3 | -2 |
|---|---|---|
| 7 | 4 | 1 |
| 5 | 5 | 7 |

FIG. 6C (Continued)

SYSTEMS AND METHODS FOR GENERATING HISTOLOGY IMAGE TRAINING DATASETS FOR MACHINE LEARNING MODELS

CROSS-REFERENCE TO RELATED APPLICATIONS

This application claims priority to U.S. Provisional Application No. 63/199,185, filed Dec. 11, 2020, which is incorporated herein by reference in its entirety.

FIELD OF THE INVENTION

The present disclosure relates to examining digital images to detect, quantify, and/or characterize cancer-related biomarker(s) and, more particularly, to detect, quantify, and/or characterize such biomarkers from analysis of one or more histopathology slide images.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Clinical success of immunotherapy cancer treatment (sometimes referred to as immuno-oncology treatment) is driving the need for new prognostic and predictive assays to inform patient selection and stratification. One way to assess potential immunotherapies is by detecting certain cell types, in a biological specimen, that may be associated with a better clinical outcome for patients (see, e.g., Chuah et al. Journal for Immunotherapy of cancer, 2019).

Commonly, immunotherapy response predictions are made based on examining immunohistochemistry (IHC) stained slides. For example, a thin slice of tumor tissue (approximately 5 microns thick) or a blood smear of cancer cells is affixed to glass microscope slides to create a histology slide, also known as a pathology slide, and that slide is submerged in a liquid solution containing an IHC stain of antibodies. Each antibody is designed to bind to one copy of the target biomarker molecule on the slide and is coupled with an enzyme that then converts a substrate into a visible dye. This stain allows a trained pathologist or other trained analyst to visually inspect the location of target molecules on the slide. Similarly, immunofluorescence (IF) is another imaging technique, one that relies upon antibodies chemically labeled with fluorescent dyes to visualize target molecules in a sample, in particular in formalin-fixed, paraffin-embedded (FFPE) specimens mounted on glass slides.

However, IHC stained slides and/or manual annotations of IHC stained slides can be costly and time consuming to generate. In addition, if only one molecule is stained in an IHC slide, it is difficult to analyze interactions between multiple molecules, which may be indicative of the likelihood of a tumor to respond to immunotherapy.

Techniques have been proposed for overcoming conventional limitations with IHC image analysis using trained machine learning models. However the number of stains that are used is limited and manual image annotation is still required for ground truth development and model training. There is a need for IHC image-informed machine learning models capable of examining histology images for tissue identification and cancer prediction.

SUMMARY OF THE INVENTION

The present application presents systems and methods of using multiplex immunohistochemistry (IHC) slide images and data to train machine learning models, in particular, to train models capable of predicting fluorescent multiplex immunochemistry (mIHC) information and immunotherapy response likelihood from histopathology images, namely Hematoxylin and eosin (H&E) slide images. In this way, techniques are provided for training learning models capable of making informative immunotherapy predictions from H&E slide images, where the training dataset includes IHC slide images. In use, these trained learning models are able to make informative immunotherapy predictions from non-stained histopathology slide images, whether H&E slide images, brightfield images, or others.

This technique may also be used to characterize subtypes of immune cells and their functional role in auto-immune diseases (for example, multiple sclerosis, lupus or SLE, type I diabetes, etc.) and inform treatment response as well as disease progression. Additional IHC and/or immunofluorescence staining (IF) stains may be used to target molecules that are not disclosed here, especially immune cell markers.

In accordance with an embodiment, a method for using a machine learning model to analyze at least one hematoxylin and eosin slide (H&E) image, the method comprising: a. receiving, at one or more processors, the H&E slide image; b. using, at the one or more processors, a machine learning model to predict locations of molecules in the H&E slide image, where the machine learning model is trained using a training data set comprising a plurality of unmarked H&E images and a plurality of marked H&E images, each marked H&E image being associated with one unmarked H&E image and each marked H&E image including a location of one or more molecules determined by analyzing a multiplex IHC image having at least two IHC stains, wherein each IHC stain has a unique color and a unique target molecule and wherein analyzing the multiplex IHC image includes determining an IHC stain that contributes to any two or more overlapping or adjacent IHC stains and comparing each IHC stain in the multiplex IHC image to a threshold; c. analyzing the number of predicted molecules and locations of the predicted molecules; and d. assigning an immunotherapy response class to the H&E slide image, based on the number of predicted molecules and/or locations of the predicted molecules.

In some examples, the molecules are immunotherapy biomarkers examples of which include CD3, CD8, CD20, CD68, CK, PD1, and PDL1.

In some examples, the method further comprises locating individual cells.

In some examples, method further comprises inferring, using a machine learning model, cell types for at least one of the individual cells.

In some examples, method further comprises predicting an immunotherapy response of the patient based, at least partially, on the inferred cell types.

In some examples, method further comprises, for each individual cell associated with two or more classes of stained molecules, calculating the proportions of each stained molecule associated with the individual cell. For example, if a cell has two or more classes of stained molecule (for example, two or more target molecules) associated with it (for example, the stained molecules appear to be located on and/or in the cell), for each class of stained molecule, a ratio, proportion, or percentage (for example, proportion or percentage of total stained molecules associated with the cell) may be calculated.

In some examples, method further comprises predicting an immunotherapy response of the patient based, at least partially, on the calculated proportions of each stained molecule associated with each individual cell.

In some examples, method further comprises calculating a multifaceted score based on imaging features and genetic features.

In some examples, method further comprises calculating additional statistics from the number of predicted molecules and locations of the predicted molecules.

In some examples, the additional statistics include at least one of: percentage of cells having a particular molecule, percentage of cells having a particular ratio of molecules, location relationships among cell types, extent of mixing of cell types, and degree of tumor infiltration by lymphocytes. In one example, a cell type may be associated with a particular ratio of molecules, or a range of ratios.

In some examples, method further comprises predicting an immunotherapy response of the patient based, at least partially, on the additional statistics.

In some examples, the assigning the immunotherapy response class includes comparing the number of predicted molecules to a threshold for each molecule.

In some examples, the assigning the immunotherapy response class includes comparing locations of predicted molecules to molecule location criteria.

In some examples, the immunotherapy response class is one of low, medium, and high lymphocyte infiltration.

In some examples, the H&E image is associated with a patient.

In some examples, method further comprises predicting an immunotherapy response of the patient, based on the number of predicted molecules and locations of the predicted molecules and matching with immunotherapy treatment.

In accordance with another embodiment, a method for using a machine learning model to analyze at least one H&E slide image associated with a patient, comprising: a. scoring H&E slide image for similarity to slide images associated with immunotherapy responders versus slide images associated with immunotherapy non-responders; and b. comparing the score to a threshold.

In some examples, the H&E image is associated with a tumor organoid.

In some examples, method further comprises predicting an immunotherapy response of the tumor organoid, based on the number of predicted molecules and locations of the predicted molecules and predicting drug sensitivity response.

In accordance with another embodiment, a method for using a machine learning model to analyze at least one hematoxylin and eosin (H&E) slide image associated with a tumor organoid, the method comprising: a. scoring a H&E slide image for similarity to slide images associated with immunotherapy responders versus slide images associated with immunotherapy non-responders; and b. comparing the score of the H&E slide image to a threshold.

In accordance with another embodiment, a method for generating training data for a histology image-based machine learning model, the method comprising: a. obtaining at least one H&E slide image associated with a biological specimen; b. obtaining one or more multiplex immunohistochemistry (IHC) images associated with the biological specimen, wherein each multiplex IHC image includes at least two IHC stains, where each IHC stain has a unique color and a unique target molecule; c. for each multiplex IHC image, detecting mixture colors comprised of more than one IHC stain and identifying the IHC stains that comprise each mixture color; d. determining the location of each IHC stain color and determining the location of the associated stained target molecules; e. detecting individual cell locations and determining which individual cells are lymphocytes; f. for each H&E image and IHC image associated with the biological specimen, align/register images such that for each physical location in the biological specimen, all pixels associated with that physical location are aligned; g. for each target molecule, marking the location on the H&E image that corresponds to the locations of the target molecules stained on the IHC layers; h. for each cell having a location that corresponds to the location of one or more IHC stains, calculating the percentage of stained pixels overlapping the cell that is associated with each IHC stain to determine an IHC stain profile for each cell; and i. storing marked and unmarked versions of the H&E image as part of a training data set.

In some examples, the H&E image is captured from a tissue layer that is stained only with H&E.

In some examples, the H&E image is captured from a tissue layer that is stained with H&E and at least one IHC stain.

In some examples, the H&E image is a virtual H&E stain image generated based on cell and tissue structures visible in a brightfield image of a tissue layer.

In some examples, determining the location of each IHC stain color includes setting an intensity threshold for each stain color and comparing the intensity of the stain color in each pixel to the intensity threshold for that stain color.

In some examples, method further comprises generating an overlay for each IHC stain where each pixel having an intensity that exceeds the threshold for the IHC stain is annotated to indicate presence of the IHC stain in the pixel.

In some examples, detecting cell locations is performed by a neural network.

In some examples, detecting cell locations includes the use of UNET.

In some examples, identifying the IHC stains that comprise each mixture color is accomplished by deconvolving mixture colors within each image.

In some examples, method further comprises assigning a tissue class to portions of the H&E image.

In some examples, method further comprises associating an immunotherapy response score with the stored unmarked H&E image, based on clinical data associated with the biological specimen.

In some examples, the immunotherapy response score is based on immunotherapy associated sequencing data, Immune Cell Infiltration, Immune Gene Expression Signatures, Multiplex PD-L1 and CD8 staining, and Multiplex macrophage IHC panels.

In some examples, the immunotherapy associated sequencing data includes tumor mutational burden (TMB), microsatellite Instability (MSI), and T Cell Clonality.

In some examples, processes (a)-(i) of the preceding method are performed for a plurality of biological specimens to generate the training data set.

In some examples, method further comprises: e. receiving the biological specimen; f. dividing the biological specimen into a plurality of tissue layers; g. simultaneously adding at least two classes of antibody-conjugated (IHC) stain to one of the tissue layers, wherein each class of antibody-conjugated stain binds to a unique class of target molecule and each class of antibody-conjugated stain has a unique stain color, such that each stain color is associated with a target molecule; and h. for each of the stained layers, capturing and storing one digital image.

In some examples, the target molecule in a first tissue layer is CD3; the target molecule in a second tissue layer is CD8; the target molecule in a third tissue layer is CD20; the target molecule in a fourth tissue layer is CD68; a fifth tissue layer is stained with H&E; the target molecules in a sixth tissue layer are CD3, CD8, CD20, CD68, CK, PD1, and PDL1; the target molecules in a seventh tissue layer are CD3, CD8, CD20, and CD68; the target molecules in an eighth tissue layer are CK, PD1, and PDL1; the target molecule in a ninth tissue layer is CK; the target molecule in a tenth tissue layer is PD1; and the target molecule in an eleventh tissue layer is PDL1.

In some examples, method further comprises simultaneously adding to one tissue layer of the tissue layers, a plurality of IHC stains such that the target molecules in the one tissue layer are CD3, CD8, CD20, CD68, CK, PD1, and PDL1.

In accordance with another embodiment, a method for training a histology image-based machine learning model, the method comprising: a. receiving a training data set comprising unmarked H&E images and data associated with each unmarked H&E image; and b. optimizing the histology image-based machine learning model to receive an unmarked H&E image and generate a simulated data set similar to the data associated with that unmarked H&E image.

In some examples, the associated data includes a corresponding marked H&E image for each unmarked H&E image, wherein the marked H&E image shows the location of IHC staining target molecules in one or more IHC images associated with the same biological specimen as the H&E image, where at least one of the IHC images is a multiplex IHC image having two or more IHC stains.

In some examples, the associated data includes an immunotherapy response score.

In some examples, method further comprises receiving the training data set of claim 1.

In some examples, method further comprises receiving the training data set of claim 14.

In some examples, the histology image-based machine learning model is a neural network.

BRIEF DESCRIPTION OF THE DRAWINGS

This patent or application file contains at least one drawing executed in color. Copies of this patent or patent application publication with color drawing(s) will be provided by the United States Patent and Trademark Office upon request and payment of the necessary fee.

The figures described below depict various aspects of the system and methods disclosed herein. It should be understood that each figure depicts an example of aspects of the present systems and methods.

FIG. 6A-6C illustrates an example neural network architecture used for tissue classification and having a fully convolution network architecture; FIG. 6B illustrates example output sizes for different layers and resulting sublayers of the architecture of FIG. 6A; and FIG. 6C is a visualization of each depth of an exemplary 3-dimensional input image matrix being convoluted by two exemplary 3-dimensional filter matrices using the architecture of FIG. 6A, for example, as may be implemented by the system of FIG. 4, in accordance with an example.

DETAILED DESCRIPTION

Figure 1:
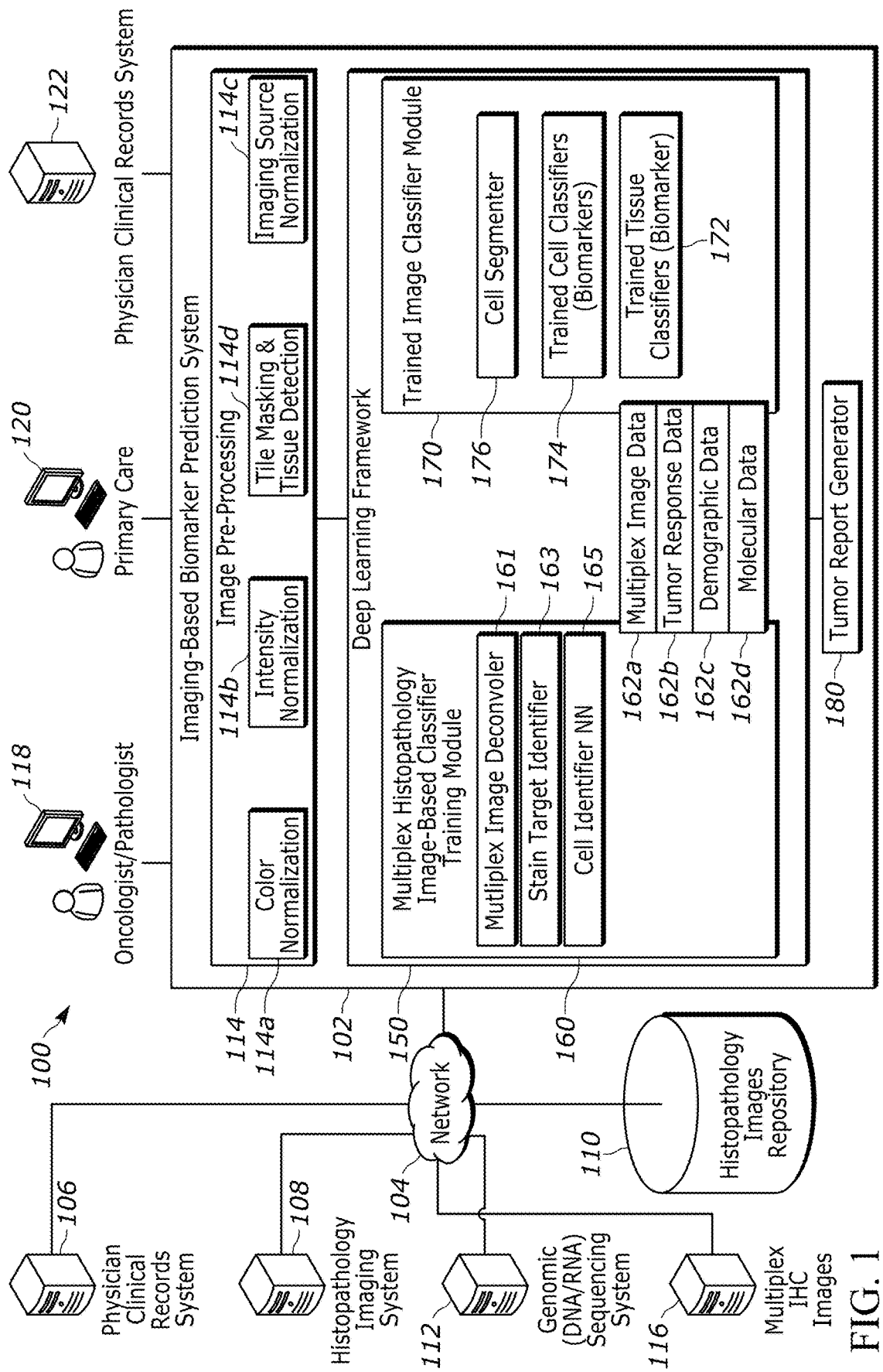
FIG. 1 illustrates a prediction system capable of analyzing digital images of histopathology slides of a tissue sample, such as H&E slide images, and determining the likelihood of biomarker presence in that tissue, in accordance with an example.

In various embodiments, the systems and methods disclosed herein annotate digital images of hematoxylin and eosin (H&E) slides with locations of immunohistochemistry (IHC) targets located in IHC stained histology slides associated with the same biological specimen as the H&E slide. In various embodiments, the systems and methods include automated processes for adding IHC labels from multiplexed IHC slide images to H&E slide images.

Multiplex imaging, such as used with multiplexed IHC slide images, allows for the assessment of multiple biomarkers from a single sample, or single slide image. In many examples, the ability to identify multiple biomarkers from a single slide is greatly advantageous over attempting to use multiple adjacent slides to detect multiple biomarkers. Different slides, even adjacent, often do not share the same cells. Moreover, even tissue may not be shared fully across adjacent slides. Indeed, by providing techniques capable of identifying and labeling locations of multiple IHC stains to be applied to H&E slide images, numerous advantages result. The present techniques can visualize multiple target antigens within a single tissue sample and even a single slice of a tissue sample, thereby maximizing the amount of data acquired from a single tissue sample. The present techniques can examine the spatial arrangements, interactions, and co-localizations of multiple proteins in a single H&E slide image. Moreover, unlike next generation sequencing techniques, image based analyses herein do not destroy tissue samples to test for individual target molecules.

In various embodiments, systems and methods are provided for using a machine learning model to analyze H&E slide images to predict locations of cells and/or molecules in the H&E slide image. Such predictions can be made alongside identification of tissue and other structures in the H&E image. In some embodiments, the machine learning models are trained using a training data set that includes (i) unmarked H&E images and (ii) marked H&E images, where those marked H&E images include location data identifying one or more molecules and where that location data is determined from an analysis of multiplex IHC images. The multiplex IHC images have at least two IHC stains, each IHC stain having a unique (i.e., different) color and a unique (i.e., different) target molecule. Moreover, the analysis of those multiplex IHC images includes determining which IHC stain(s) contribute to two or more overlapping/adjacent IHC stains thereby allowing for molecule identification across different stains. With the machine learning models trained using multiplex IHC, in this way, these models may then be used to analyze molecules and locations in H&E slide images and assign an immunotherapy response class to the H&E slide image.

In various embodiments, the H&E slide images fed to trained machine learning models can be virtual, e.g., based on a brightfield image. In some examples, the H&E slide images are generated by adding H&E stains to a tissue slice having multiple IHC stains, on top of the mIHC stains. In some examples, a tissue slice with multiple IHC stains is washed to remove the IHC stains and then H&E stains are added to the tissue slice to generate the H&E slide images.

In various embodiments, the machine learning models herein are trained using ground truth annotated images, in particular ground truths developed from multiplex IHC images. The recent advance of computational pathology systems has enabled the identification of immune-related biomarkers (termed immunotherapy biomarkers) and a detailed understanding of the tumor microenvironment. Examples of biomarkers being explored in immunotherapy (immunotherapy biomarkers) include serum proteins, tumor-specific receptor expression patterns, factors in the tumor microenvironment, circulating immune and tumor cells, and host genomic factors. Such systems can identify and quantify different immune cell subsets, their spatial context, and the expression of immune checkpoint markers, albeit with degrees of accuracy. Building computational pathology systems is facilitated by having large-scale, high-quality ground truth annotations.

Therefore, in various embodiments, the systems and methods herein include generating ground truth annotated images. In some examples, these techniques include staining, digitizing, and analyzing brightfield multiplex (Mx) FFPE tissue slides to generate ground truth annotations. More generally, systems and methods may generate multiplex-derived annotations, which may be used to train and quantitatively validate a machine learning model trained for histology tissue segmentation and cell detection of H&E slide images.

FIG. 1 illustrates a prediction system 100 capable of analyzing digital images of histopathology slides of a tissue sample, such as H&E slide images, and determining the likelihood of biomarker presence in that tissue, where biomarker presence indicates a predicted tumor presence, a predicted tumor state/condition, or other information about a tumor of the tissue sample, such as a possibility of clinical response through the use of a treatment associated with the biomarker or predicted tumor state/condition.

The system 100 includes an imaging-based biomarker prediction system 102 that implements, among other things, image processing operations, deep learning frameworks, and report generating operations to analyze histopathology images of tissue samples and predict the presence of biomarkers in the tissue samples. In various examples, the system 100 is configured to predict the present of these biomarkers, tissue location(s) associated with these biomarkers, and/or cell location of these biomarkers.

Figure 12:
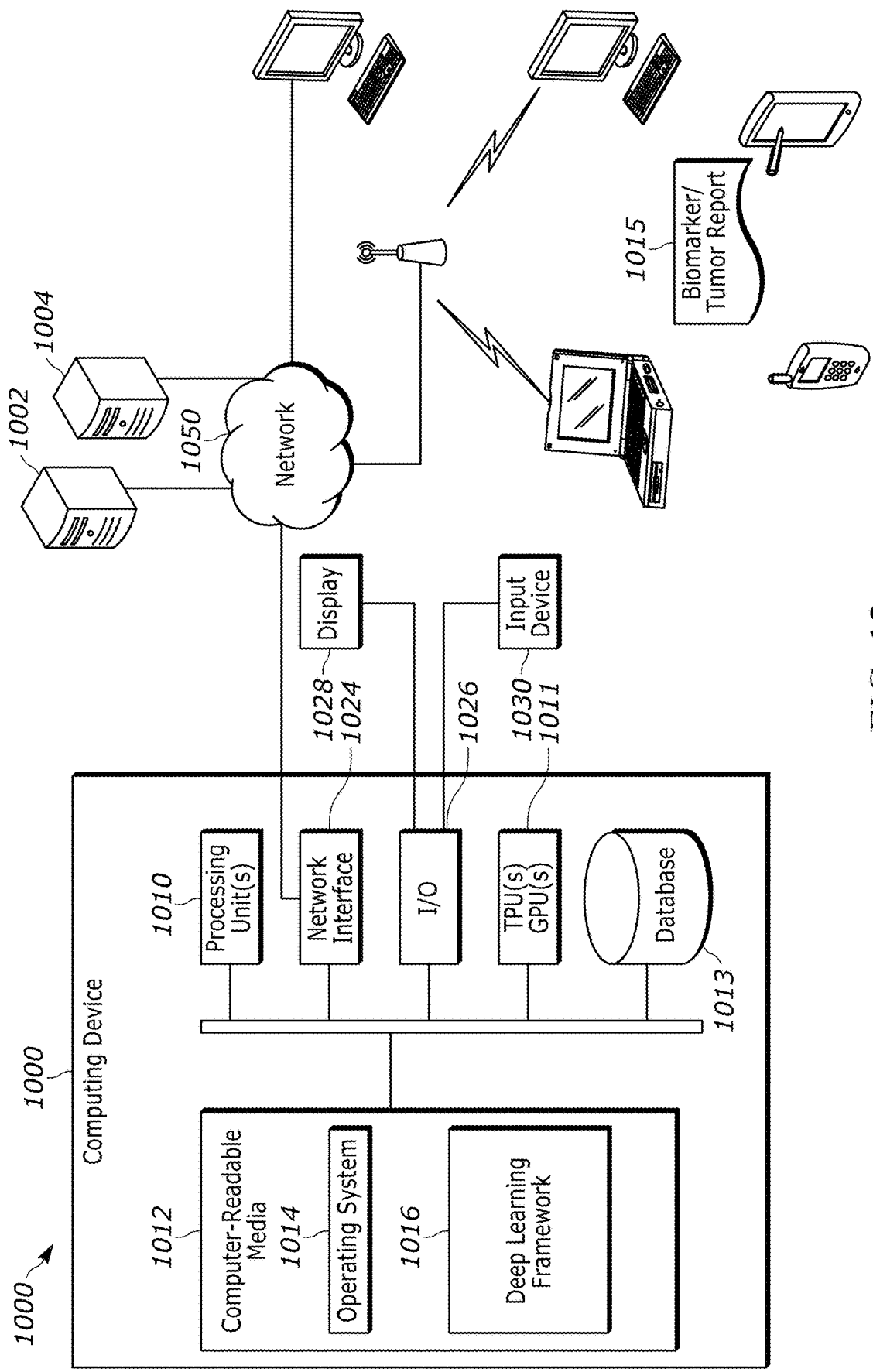
FIG. 12 illustrates an example computing device for implementing the imaging-based biomarker prediction system of FIGS. 1 and 11 and other systems herein, in accordance with an example.

The imaging-based biomarker prediction system 102 may be implemented on one or more computing devices, such as a computer, tablet or other mobile computing device, or server, such as a cloud server. The imaging-based biomarker prediction system 102 may include a number of processors, controllers or other electronic components for processing or facilitating image capture, generation, or storage and image analysis, and deep learning tools for analysis of images, as described herein. An example computing device 1000 for implementing the imaging-based biomarker prediction system 102 is illustrated in FIG. 12.

As illustrated in FIG. 1, the imaging-based biomarker prediction system 102 is connected to one or more medical data sources through a network 104. The network 104 may be a public network such as the Internet, private network such as a research institution's or corporation's private network, or any combination thereof. Networks can include, local area network (LAN), wide area network (WAN), cellular, satellite, or other network infrastructure, whether wireless or wired. The network 104 can be part of a cloud-based platform. The network 104 can utilize communications protocols, including packet-based and/or datagram-based protocols such as internet protocol (IP), transmission control protocol (TCP), user datagram protocol (UDP), or other types of protocols. Moreover, the network 104 can include a number of devices that facilitate network communications and/or form a hardware basis for the networks, such as switches, routers, gateways, access points (such as a wireless access point as shown), firewalls, base stations, repeaters, backbone devices, etc.

Via the network 104, the imaging-based biomarker prediction system 102 is communicatively coupled to receive medical images, for example of histopathology slides such as digital H&E stained slide images, multiplex and single-plex IHC stained slide images, or digital images of any other staining protocols from a variety of different sources. These sources may include a physician clinical records systems 106 and a histopathology imaging system 108. Any number of medical image data sources could be accessible using the system 100. The histopathology images may be images captured by any dedicated digital medical image scanners, e.g., any suitable optical histopathology slide scanner including 10×, 20×, and/or 40× resolution magnification scanners. Further still, the biomarker prediction system 102 may receive images from histopathology image repositories 110. In yet other examples, images may be received from a partner genomic sequencing system 112, e.g., the TCGA and NCI Genomic Data Commons. In the illustrated example, the biomarker prediction system 102 may receive multiplex IHC images from an imaging source 116. These image sources may communicate image data, genomic data, patient data, treatment data, historical data, etc., in accordance with the techniques and processes described herein. Each of the image sources may represent multiple image sources. Further, each of these image sources may be considered a different data source, those data sources may be capable of generating and providing imaging data that differs from other providers, hospitals, etc. The imaging data between different sources potentially differs in one or more ways, resulting in different data source-specific bias, such as in different dyes, biospecimen fixations, embeddings, staining protocols, and distinct pathology imaging instruments and settings.

In the example of FIG. 1, the imaging-based biomarker prediction system 102 includes an image pre-processing sub-system 114 that performs initial image processing to enhance image data for faster processing in training a machine learning framework and for performing biomarker prediction using a trained deep learning framework. Such image pre-processing may include performing a normalization process on received image data, including one or more of color normalization 114a, intensity normalization 114b, and imaging source normalization 114c, to compensate for and correct for differences in the received image data. While in some examples the imaging-based biomarker prediction system 102 receives medical images, in other examples the sub-system 114 is able to generate medical images, including multiplex IHC images, either from received histopathology slides or from other received images, such as generating composite histopathology images by aligning shifted histopathology images to compensate for vertical/horizontal shift. This image pre-processing allows a deep learning framework to more efficiently analyze images across large data sets (e.g., over 1000s, 10000s, to 100000s, to 1000000s of medical images), thereby resulting in faster training and faster analysis processing.

The image pre-processing sub-system 114 may perform further image processing that removes artifacts and other noise from received images by doing tile mask application and tile-specific tissue detection 114d, for example, to identify regions of the images corresponding to tissue for subsequent analysis, classification, and segmentation. For example, as further described herein, in multiscale configurations where image data is to be analyzed on a tile-basis, the masking & detection sub-system 114d may receive an initial histopathology image, at a first image resolution, downsampling that image to a second image resolution, and then performing a normalization on the downsampled histopathology image, such as color and/or intensity normalization, and removing non-tissue objects from the image, and then apply a tile mask to generate tiles representing sub-sections of the received images.

The imaging-based biomarker prediction system 102 may be a standalone system interfacing with the external (i.e., third party) network-accessible systems 106, 108, 110, 112, and 116. In some examples, the imaging-based biomarker prediction system 102 may be integrated with one or more of these systems, including as part of a distributed cloud-based platform. For example, the system 102 may be integrated with a histopathology imaging system, such as a digital H&E stain imaging system, e.g. to allow for expedited biomarker analysis and reporting at the imaging station. Indeed, any of the functions described in the techniques herein may be distributed across one or more network accessible devices, including cloud-based devices.

In some examples, the imaging-based biomarker prediction system 102 is part of a comprehensive biomarker prediction, patient diagnosis, and patient treatment system. For example, the imaging-based biomarker prediction system 102 may be coupled to communicate predicted biomarker information, tumor prediction, and tumor state information to external systems, including a computer-based pathology lab/oncology system 118 that may receive a generated biomarker report including image overlay mapping and use the same for further diagnosing cancer state of the patient and for identifying matching therapies for use in treating the patient. The imaging-based biomarker prediction system 102 may further send generated reports to a computer system 120 of the patient's primary care provider and to a physician clinical records system 122 for databasing the patients report with previously generated reports on the patient and/or with databases of generated reports on other patients for use in future patient analyses, including deep learning analyses, such as those described herein.

To analyze the received histopathology image data and other data, the imaging-based biomarker prediction system 102 includes a deep learning framework 150 that implements various machine learning techniques to generate trained classifier models for image-based biomarker analysis from received training sets of image data or sets of image data and other patient information. With trained classifier models, the deep learning framework 150 is further used to analyze and diagnose the presence of image-based biomarkers in subsequent images collected from patients. In this manner, images and other data of previously treated and analyzed patients is utilized, through the trained models, to provide analysis and diagnosis capabilities for future patients.

In various embodiments, the deep learning framework 150 includes a multiplex histopathology image-based classifier training module 160 that can access received and stored images and data from the external systems 106, 108, 110, 112, and 116, and any others, where that data may be parsed from received data streams and databased into different data types. The different data types may be divided into image data 162a which may be associated with the other data types molecular data 162b, demographic data 162c, and tumor response data 162d. An association may be formed by labeling the image data 162a with one or more of the different data types. By labeling the image data 162a according to associations with the other data types, the imaging-based biomarker prediction system may train an image classifier module to predict the one or more different data types from image data 162a.

In various embodiments herein, and as discussed further herein, the image data 162a may be multiplex histology images, such as one or more multiplex IHC stain images. As discussed further herein, the multiplex classifier training module 160 may include a multiplex image deconvolver 161, a stain image target identifier 163, and a cell identifier neural network 165.

In the illustrated data, the deep learning framework 150 includes image data 162a. For example, to train or use a multiscale PD-L1 biomarker classifier, this image data 162a may include pre-processed image data received from the sub-system 114, images from H&E slides or images from IHC slides (with or without human annotation), including IHC slides targeting PD-L1. The IHC slides may include additional targets, for example, PTEN, EGFR, Beta catenin/catenin beta1, NTRK, HRD, PIK3CA, and hormone receptors including HER2, AR, ER, and PR. To train or use other biomarker classifiers, whether multiscale classifiers or single-scale classifiers, the image data 162A may include images from other stained slides. Further, in the example of training a single scale classifier, the image data 162A is image data associated with RNA sequence data for particular biomarker clusters, to allow the multiple instance learning (MIL) techniques herein.

The molecular data 162b may include DNA sequences, RNA sequences, metabolomics data, proteomic/cytokine data, epigenomic data, tumor organoid data, raw karyotype data, transcription data, transcriptomics, microbiomics, and immunomics, identification of variants (for example, SNP, MNP, InDel, microsatellite Instability (MSI), tumor mutational burden (TMB), CNV Fusions, loss of heterozygosity, loss or gain of function). Epigenomic data includes DNA methylation, histone modification, or other factors which deactivate a gene or cause alterations to gene function without altering the sequence of nucleotides in the gene. Microbiomics includes data on viral infections which may affect treatment and diagnosis of certain illnesses as well as the bacteria present in the patient's gastrointestinal tract which may affect the efficacy of medicines ingested by the patient or other clinical characteristics of the patient. Proteomic data includes protein composition, structure, and activity; when and where proteins are expressed; rates of protein production, degradation, and steady-state abundance; how proteins are modified, for example, post-translational modifications such as phosphorylation; the movement of proteins between subcellular compartments; the involvement of proteins in metabolic pathways; how proteins interact with one another; or modifications to the protein after translation from the RNA such as phosphorylation, ubiquitination, methylation, acetylation, glycosylation, oxidation, or nitrosylation.

The deep learning framework 150 may further include demographic data 162c and tumor response data 162d (including data about a reduction in the growth of the tumor after exposure to certain therapies, for example immunotherapies, DNA damaging therapies like PARP inhibitors or platinums, or HDAC inhibitors). The demographic data 162c may include age, gender, race, national origin, etc. The tumor response data 162d may include epigenomic data, examples of which include alterations in chromatin morphology and histone modifications.

The tumor response data 162d may include cellular pathways, example of which include IFNgamma, EGFR, MAP KINASE, mTOR, CYP, CIMP, and AKT pathways, as well as pathways downstream of HER2 and other hormone receptors. The tumor response data 162d may include cell state indicators, examples of which include Collagen composition, appearance, or refractivity (for example, extracellular vs fibroblast, nodular fasciitis), density of stroma or other stromal characteristics (for example, thickness of stroma, wet vs. dry) and/or angiogenesis or general appearance of vasculature (including distribution of vasculature in collagen/stroma, also described as epithelial-mesenchymal transition or EMT). The tumor response data 162d may include tumor characteristics, examples of which include the presence of tumor budding or other morphological features/characteristics demonstrating tumor complexity, tumor size (including the bulky or light status of a tumor), aggressiveness of tumor (for example, known as high grade basaloid tumor, especially in colorectal cancer, or high grade dysplasia, especially in barrett's esophagus), and/or the immune state of a tumor (for example, inflamed/"hot" vs. non-inflamed/"cold" vs immune excluded).

The multiplex histopathology image-based classifier training module 160 may be configured with an image-analysis adapted machine learning techniques, including, for example, deep learning techniques, including, by way of example, a CNN model and, more particular, a tile-resolution CNN, that in some examples is implemented as a FCN model, and, more particularly still, implemented as a tile-resolution FCN model. Any of the data types 162a-162d may be obtained directly from data communicated to the imaging-based biomarker prediction system 102, such as contained within and communicated along with the histopathology images. The data types 162a-162d may be used by the histopathology image-based classifier training module 160 to develop classifiers for identifying one of more of the biomarkers discussed herein, such as immunotherapy biomarkers.

In the example system 100, the deep learning framework 150 further includes a trained image classifier module 170 that may also be configured with the deep learning techniques, including those implementing the module 160. In some examples, the trained image classifier module 170 accesses the image data 162 for analysis and biomarker classification. In some examples, the module 170 further accesses the molecular data 162, the demographic data 162c, and/or tumor response data 162d for analysis and tumor prediction, matched therapy predictions, etc.

The trained image classifier module 170 includes trained tissue classifiers 172, trained by using ground truth mask images and other data from the module 160, using one or more training image sets, to identify and classify tissue type in regions/areas of received image data.

The module 170 also includes trained cell classifiers 174 that identify immunotherapy biomarkers via cell classification in received histology images, e.g., in unmarked H&E slide images. The module 170 may further include a cell segmenter 176 that identifies cells within a histopathology image, including cell borders, interiors, and exteriors, albeit in some examples, the cell segmentation is a trained model of the cell classifier 174.

In examples herein, the tissue classifiers 172 may include biomarker classifiers specifically trained to identify tumor infiltration (such as by ratio of lymphocytes in tumor tissue to all cells in tumor tissue), lymphocyte infiltration (high, medium, or low), PD-L1 (such as positive or negative status), ploidy (such as by a score), CMS (such as to identify subtype), NC Ratio (such as nucleus size identification), signet ring morphology (such as a classification of a signet cell or vacuole size), HRD (such as by a score, or by a positive or negative classification), etc. in accordance with the immunotherapy biomarkers herein. It will be appreciated that lymphocyte infiltration is a type of tumor infiltration.

As detailed herein, the trained image classifier module 170 and associated classifiers may be configured with an image-analysis adapted machine learning techniques, including, for example, deep learning techniques, including, by way of example, a CNN model and, more particular, a tile-resolution CNN, that in some examples is implemented as a FCN model, and, more particularly still, implemented as a tile-resolution FCN model, etc.

The system 102 further includes a tumor report generator 180 configured to receive classification data from the trained tissue (biomarker) classifiers 172, the trained cell (biomarker) classifiers 174 and the cell segmenter 172 and determine tumor metrics for the image data and generate digital image and statistical data reports, where such output data may be provided to the pathology lab 118, primary care physician system 120, genomic sequencing system 112, a tumor board, a tumor board electronic software system, or other external computer system for display or consumption in further processes. In various examples, the tumor report generator 180 receives the classification data and calculates various statistics, including one or more of percentage of cells having a particular molecule, percentage of cells having a particular ratio of molecules, location relationships among cell types, extent of mixing of cell types, degree of tumor infiltration by lymphocytes (high, medium, or low), and/or other statistics herein. The report generator 180 may calculate these statistics from the number of predicted molecules and locations of the predicted molecules contained in the classification data. In some implementations, these statistics are determined by a machine learning model, such as machine learning model 304.

Figure 2:
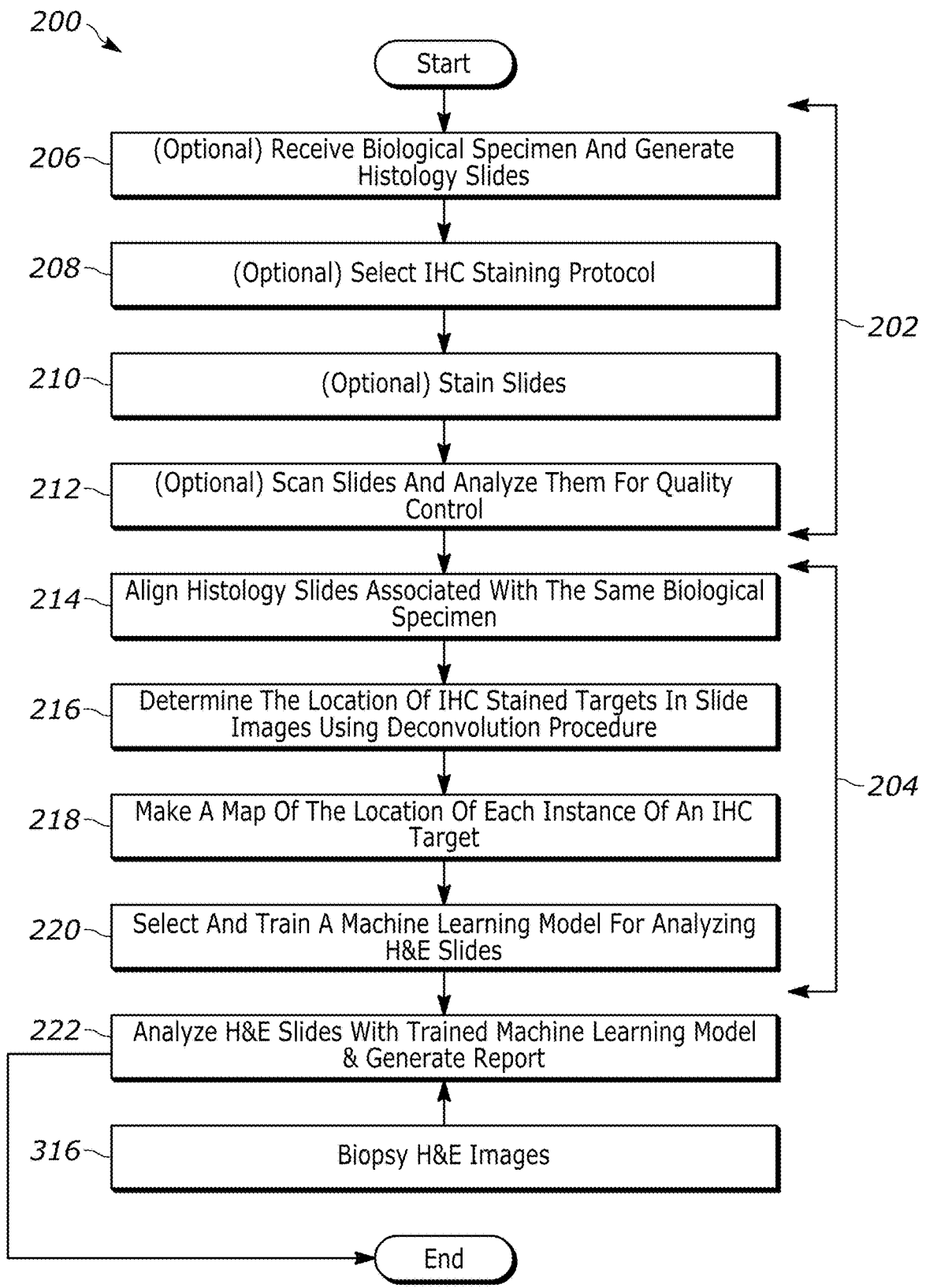
FIG. 2 illustrates a process of analyzing digital images of histopathology slides of a tissue sample using a trained machine learning model as may be performed by the prediction system of FIG. 1, in accordance with an example.

In various embodiments, the imaging-based biomarker prediction system 102 is configured to train machine learning models to analyze H&E slide images, where that training is based on received multiplex IHC stained images. In an example, a process 200, in FIG. 2, is provided for training a machine learning model and analyzing H&E slide images using that trained machine learning to assist in determination of an immunotherapy response for a subject. In the illustrated example, the process 200 is implemented in two stages, an optional multiplex IHC staining stage 202 and a machine learning training stage 204.

In an example implementation of the multiplex IHC staining stage 202, at a process 206 a biological specimen is received and histology slides are generated. The biological specimen may be taken from a biopsy, bone marrow biopsy, endoscopic biopsy, needle biopsy (e.g., fine-needle aspiration, core needle, vacuum-assisted, image-guided), skin biopsy (e.g., shave, punch, incisional, excisional), surgical biopsy, etc. The process 206 may further include dividing the received biological specimen into a plurality of tissue layers, known as slices, where the slices may be approximately 4-13 microns thick.

At a process 208, a staining protocol is selected for use on each of the slices. In various embodiments, the staining protocol includes identification of the biological specimens that will be stained, such as specimen tissue source, organ source, etc. and/or other data. The staining protocol may further include identification of the type of staining equipment (for example, stainer) to be used including strainers capable of multiplex IHC staining. The staining protocol may further include IHC targets for each tissue slice (or if the tissue slice will be H&E stained), the antibody to use for each IHC target, the chromogen to use for each IHC target, and the order in which each target will be stained (for multiplexed IHC staining). Conventional slice preparation techniques may be included, as well as post-staining steps for imaging analysis. In various embodiments, IHC targets may be various molecules, for example, proteins, RNA, DNA, lipids, sugars, or any molecule that can be bound by a stain-conjugated antibody or stained by other means of cellular staining. In some examples, the IHC staining protocol is selected based on any of the foregoing data. In various embodiments, at the process 208, the IHC staining protocol is selected and optimized. An example optimization is described further according to Example 1.

In an embodiment, one of the slices from process 206 is stained with H&E and at least one of the other slices is stained with multiple classes of IHC antibodies, to form an multiplex IHC (mIHC) slide. To generate the multiplex slide, at least two classes of antibody-conjugated (IHC) stain are applied to a tissue layer, wherein each class of antibody-conjugated stain binds to a unique class of target molecule and each class of antibody-conjugated stain has a unique stain color, such that each stain color is associated with a target molecule. In various examples, preferably 2-10 antibody-conjugated IHC stains are applied to form a mIHC stain. That is, in various examples 2, 3, 4, 5, 6, 7, 8, 9, or 10 IHC stains may be applied to a slice to form an mIHC stain slice. Optionally, to include additional slice images in the training dataset, for each remaining slice, at least one class of antibody-conjugated stain is added to the slice. In some examples, the training dataset may be based on having multiple multiplex IHC stain images.

In this way, in various embodiments, the systems and methods add multiple antibodies to the same slide simultaneously, at a process 210 at which the slices are stained according to the selected IHC staining protocol. If the antibodies are from different species, there may be intermediate steps when adding these antibodies at process 210. In various embodiments, however, the addition of DAB or heptane to block antibodies between any intermediate steps may not be required. Moreover, by using multiple IHC staining, techniques herein do not require cyclic staining and are likely to cause tissue degradation. That is, unlike conventional techniques that require various cyclic immunofluorescence (IF) and immunohistochemical (IHC) methods using cycles of fluorescent tagging, imaging and bleaching or dissociation of the affinity tags to improve spectral resolution of immunostaining, the present techniques can train machine learning models without needing to serially image a sample that is re-stained many times.

While IHC staining protocol selection may be partially manually performed, in some examples, the process 210 applies an automated procedure to stain the slices according to the staining protocol. Automation allows standardizing the staining process to reduce variability and improve staining quality, reproducibility, and speed. For example, this may include using a Ventana DISCOVERY ULTRA Research autostainer. (see diagnostics.roche.com/us/en/products/instruments/discovery-ultra).

In the illustrated example, at a process 212, the staining slides are scanned using a slide imager and the resulting H&E slide image and multiplex IHC slide image(s) and any single IHC slide images are analyzed using image processing to perform an image quality assessment. In an example, slide images may be scanned at 40× magnification with the Philips IntelliSite Pathology Solution Ultra Fast Scanner. Slide images that do not pass image quality assessment post-scan (for example, slide images that are out of focus) will be rejected by the process 212, discarded, and the imager automatically instructed to rescan the slide. Slide images that satisfy the image quality assessment, will be passed to the machine learning training process 204.

Therefore, in the illustrated example, the processes 206-212 form the IHC staining process 202 from which control is passed to the machine learning training process 204. Alternatively, multiplex IHC image(s), H&E slide image(s), and single IHC image(s) of scanned slides may be received directly to the process 204 and the optional procedures of process 202 avoided.

To train machine learning models, the process 204 automatically locates IHC targets within mIHC slide images to generate training data. At a process 214, histology slide images associated with the same biological specimen are aligned, including the H&E and multiplex IHC stain images. In various embodiments, the process 214 register the histology images, by digitally aligning images such that they reflect the relative 3-dimensional position of the tissue before the specimen was sliced into tissue layers. In an example, the process 214 may overlay a digital location grid on each histology image (i.e., on each H&E stain and multiple IHC and single IHC associated with the sample) such that a location coordinate on that grid is associated with corresponding (stacked) locations on all slides for a biological specimen. Next, the process 214 may apply a global alignment. In an example, all IHC slides (single and multiplex) may be co-registered with the H&E tissue slide. A tissue segmentation may be performed and then a global rigid registration (e.g., an affine transform) may be applied to consecutive slides to align tissues at a sufficient threshold magnification, such as at 10× magnification. Further still, at the process 214 a local alignment (e.g., a per-patch non-linear registration) may be applied at a sufficient threshold magnification, typically larger than the rigid registration magnification (e.g., 20× magnification), using normalized gradient fields. This local alignment may be useful for cell-to-cell comparisons across serial sections in the histology images, to perform a cell-level registration. In some embodiments, the registration algorithm's performance may be determined via a qualitative review of different field-of-views randomly sampled within the H&E tissue region.

In various embodiments, location and molecular and cell data is developed across the different histology images to develop the training dataset. In the illustrated example, a process 216 determines the location of ICH stained targets in all histology slide images, including in the H&E slide images, and by using a deconvolving process to resolve cells and molecules co-extensive across multiple IHC stains. Whether multiplex or single stain, IHC stained targets include molecules, cell markers, other cell components. The process 216 identifies the multiplex IHC images and deconvolves any overlapping stain colors. That is, multiple colors may overlap on IHC stained slides having more than one IHC target/multiplexed IHC targets. Color deconvolution facilitates detection of two or more co-localized antibodies (for example, two or more antibodies located in close proximity or in the same location on a slide) and thus the detection of two or more co-localized target molecules bound to the antibodies. An example, deconvolution process is described in Haub, P., Meckel, T. A, Model based Survey of Colour Deconvolution in Diagnostic Brightfield Microscopy: Error Estimation and Spectral Consideration, Sci. Rep 5, 12096 (2015) doi.org/10.1038/srep12096), the contents of which are incorporated herein by reference in their entirety.

In various embodiments, to perform deconvolution, the process 216 is configured to determine spectral absorbance/transmittance values at different wavelengths and across the multiplex IHC image. In particular, the process 216 is configured to apply a procedure built upon the Bouguer-Lambert-Beer equation, which describes the absorption of monochromatic radiation passing absorbing dyes:

$$I(\lambda) = I_0(\lambda) \cdot e^{-\delta(\lambda) \cdot c} \quad (1)$$

where $I_0(\lambda)$ is the spectral radiation intensity, $I(\lambda)$ is the transmitted spectral intensity, $\delta(\lambda)$ is the spectral molar optical density for a unified layer thickness, and c is the dye concentration.

For two or more stains i located close enough to each other that they combine to appear as a mixture color, a spectral absorbance $A(\lambda)$ can be expressed as:

$$A(\lambda) = -\ln\left(\frac{I(\lambda)}{I_0(\lambda)}\right) = \sum_i (\delta_i(\lambda) \cdot c_i) \quad (2)$$

With known spectral absorbance values Ajip for different pure stains i, a set of linear equations can be formulated to express the spectral absorbance Aj for different wavelength j, e.g., for two wavelengths k and l and two pure stains, as:

$$A_k = A_{k1p} \cdot c'_1 + A_{k2p} \cdot c'_2 \quad (3)$$

$$A_l = A_{l1p} \cdot c'_1 + A_{l2p} \cdot c'_2 \quad (4)$$

Thus, in some examples, the process 216 uses these linear equations to 'unmix' measured absorbance values Aj by calculating the relative concentrations c'1 and c'2. This approach can be extended to higher orders of wavelengths and stains, i.e., where more than 2 stains are used to form the multiplex IHC. In some examples, the process 216 may receive IHC staining data, such as from the IHC staining protocol identified at 208. In some examples, the process 216 may apply a brute-force method of analyzing receiving IHC images at multiple different wavelengths, assessing spectral absorption/transmittance from which the process identifies between multiplex IHC images and single IHC images and from which the process determines the number of IHC stains in the multiplex IHC image and the stain types (including associated absorption wavelengths).

A stain vector $\vec{A}_{ip}$ describes the absorbance characteristics of a pure stain i and is expressed, for example, for two monochromatic wavelengths k and l by the stains spectral transmittance $\tau p(\lambda)$:

$$\vec{A}_{ip} = \begin{pmatrix} A_{kip} \\ A_{lip} \end{pmatrix} = \begin{pmatrix} -\ln\left(\frac{I_{ip}(\lambda_k)}{I_0(\lambda_k)}\right) \\ -\ln\left(\frac{I_{ip}(\lambda_l)}{I_0(\lambda_l)}\right) \end{pmatrix} = \begin{pmatrix} -\ln(\tau_{ip}(\lambda_k)) \\ -\ln(\tau_{ip}(\lambda_l)) \end{pmatrix} \quad (5)$$

Stain vectors define the target coordinate system for the linear transformation from absorbance into concentration space. The process 216, thus, may specify stain vectors prior to the deconvolution, where these stain vectors can be estimated from samples ideally stained with pure dyes.

If normalized stain vectors with a unit length of 1 are used for unmixing, the resulting normalized relative concentration values c* are related to relative concentration c' by:

$$c'_i = \frac{c*i}{|\vec{A}_{ip}|} \quad (6)$$

In some diagnostic brightfield applications of the techniques herein, the absorbance values used for stain vector estimation and color deconvolution (CD), are calculated from the sensor signals VR, VG, VB measured with scientific RGB color cameras in a slide imager. For a typical RGB camera with 8 bit maximum color channel values V0R, V0G, V0B this can be formulated (without considering any disruptive imaging effects) as:

$$A_R = -\ln\left(\frac{V_R}{V_{0R}}\right) = -\ln\left(\frac{V_R}{255}\right) \quad (7)$$

$$A_G = -\ln\left(\frac{V_G}{V_{0G}}\right) = -\ln\left(\frac{V_G}{255}\right) \quad (8)$$

$$A_B = -\ln\left(\frac{V_B}{V_{0B}}\right) = -\ln\left(\frac{V_B}{255}\right) \quad (9)$$

In some embodiments, the process 216 models the formation of non-monochromatic camera signals V'R, V'G, V'B by summation of spectral products of light intensity Irel(λ), stain transmittance τp(λ) and the sensor characteristics sR(λ), sG(λ), sB(λ). For two stains, for example, this modeling is as follows:

$$V'_R = \sum_{j=1...60} (I_{rel}(\lambda_j) \cdot \tau_{1p}(\lambda_j)^{c1} \cdot \tau_{2p}(\lambda_j)^{c2} \cdot s_R(\lambda_j)) \quad (10)$$

$$V'_G = \sum_{j=1...60} (I_{rel}(\lambda_j) \cdot \tau_{1p}(\lambda_j)^{c1} \cdot \tau_{2p}(\lambda_j)^{c2} \cdot s_G(\lambda_j)) \quad (11)$$

$$V'_B = \sum_{j=1...60} (I_{rel}(\lambda_j) \cdot \tau_1(\lambda_j)^{c1} \cdot \tau_2(\lambda_j)^{c2} \cdot s_B(\lambda_j)) \quad (12)$$

with λ1 ... λ60={405 nm, 410 nm, ... 700 nm}.

Maximum camera values V'0R, V'0G, V'0B were calculated without staining (c'1=c'2=0). Based on these equations the non-linear signal formation is simulated to evaluate the deconvolution of absorbance values derived from these signals.

After deconvolution, the IHC slide image data is analyzed to identify the location of IHC stained targets in the multiplex IHC image, including IHC stained targets identified by each different IHC stain type of the IHC stained targets coinciding with multiple stain types. That is, the deconvolution is used to determine an IHC stain that contributes to any two or more overlapping/adjacent IHC stains. Next, at a process 218, a map of the locations of each instance of the IHC stain target is determined. For example, each IHC stain in the multiplex IHC image may be compared to one or more threshold to determine locations of IHC stained targets. From this, the predicted IHC stain targets, e.g., the predicted molecules, are identified along with their location in the IHC stain images.

In various embodiments, the process 218 apply a binary mask at the pixel level. For example, each pixel may be assigned a value of "1" indicating the pixel as the color associated with the IHC target or "0" indicating the pixel does not have a staining color. A wavelength specific threshold absorption value may be applied as the binary mask. In some embodiments, the process 218 determines a field of view (FOV) of the histology images before apply the binary mask. For example, a FOV may be identified that contains a minimum number of cells, where that minimum number has been selected by the user through a graphical user interface. In some examples, binary masks are obtained for each marker using color deconvolution and intensity-based thresholding on a select set of fields of view (FOVs). Each FOV should contain a minimum of x stained cells, where x may be 5, 10, 15, or 20, for example. Further still, in some examples, the threshold applied by the binary masks may be adjusted by a user through a graphic user interface.

In various embodiments, in addition to the deconvolution and mapping analysis of the stain overlapping regions of an multiplex IHC described above, binary masks may be determined from analyzing the single stain (non-overlapping) regions of these images or of single IHC stain images. For example, manually corrected masks may be obtained from single stain sections of IHC images and applied to a machine learning model to predict multiclass masks from multiplex IHC images.

With the multiplex IHC images mapped and locations of IHC stain targets identified across single stain and overlapping stain regions of the multiplex IHC image, at a process 220, a machine learning model is selected and train to analyze H&E input slides for predicting molecules and molecule location in those H&E slides, for ultimately assigning an immunotherapy response class to the H&E slide image.

In various embodiments, at the process C20, a machine learning model may be trained for cell detection, cell classification, and/or tissue segmentation of digital H&E stained slide images. In an example, co-registered H&E and multiplex IHC images, or FOVs, are used to train an H&E cell detection model with ground truth masks derived from the multiplex IHC slides images. Further still, the, the machine learning model may be trained to detect and ignore biological artifacts (for example, necrotic cells, mucin, etc.). While shown as part of the process 200, in some implementations the training of the machine learning model may be performed separately from the process 200.

With the machine learning model trained, at a process 222 the training machine learning model is used to analyze one or more H&E slide images. For example, at the process 222, a new H&E slide image associated with patient biopsy, blood sample, or tumor organoid is received and analyze with trained machine learning model.

The process 222 may be configured to report results of that analysis, where the report may include a digital visual indication of the locations of target molecules, immune and/or cancer cell types in slide image. In some examples, the report may include a degree of mixing of cell types, tumor infiltration, and/or immune infiltration detected in slide image. In some examples, the report may include data on the likelihood that the patient or tumor organoid will respond to immunotherapy, i.e., the assigning of an immunotherapy response class. In examples herein, immunotherapy may include ipilimumab, atezolizumab, avelumab, durvalumab, nivolumab, pembrolizumab, anti-PD-L1 therapies, checkpoint inhibitors, axicabtagene ciloleucel, tisagenleleucel, CAR T-cell therapies, any combination thereof, etc. For example, immunotherapies are described in archivesofpathology.org/doi/full/10.5858/arpa.2018-0584-CP, the contents of which are incorporated herein by reference in their entirety for any and all purposes.

In various applications the process 200 can be used for early stage clinical trials, where histology image data for training is relatively small. By using multiplex IHC stain images and the deconvolution processes here, allowing for identification of molecules and molecular location in overlapping stain regions, a few number of tissue slices may be used to train a robust machine learning model. Further that multiplex IHC stain images are used to train a machine learning model operating on H&E stain images, allows for faster analysis and immunology response prediction, through the ability to identify not on conventional structural features in an H&E image but various different types of molecules and molecule location. Thus, the process 200 allows for pharmacologic research to be deployed with machine learning techniques, even at the earliest stages to identify candidate responders and candidates for adverse events (resistance, recurrence, etc.) responsive to different immunotherapies.

In various embodiments, the report generated by the process 222 may include immune contexture profiling. In various examples, the process 222 generates a cancer immunogram as a report for individualized prediction of immunotherapy response. In some examples, the process 222 generates integrates gene sequencing data for further analysis. For example, the process 222 can identify specific PD1-positive subpopulations in NSCLC via integration of RNAseq analysis and multiplex imaging. Thus, in some examples, the process 222 provides a trained computational pathology machine learning model that identifies PD1 T cells in pre-treatment biopsies from H&E stain images and correlates with treatment response to immune checkpoints.

Figure 3:
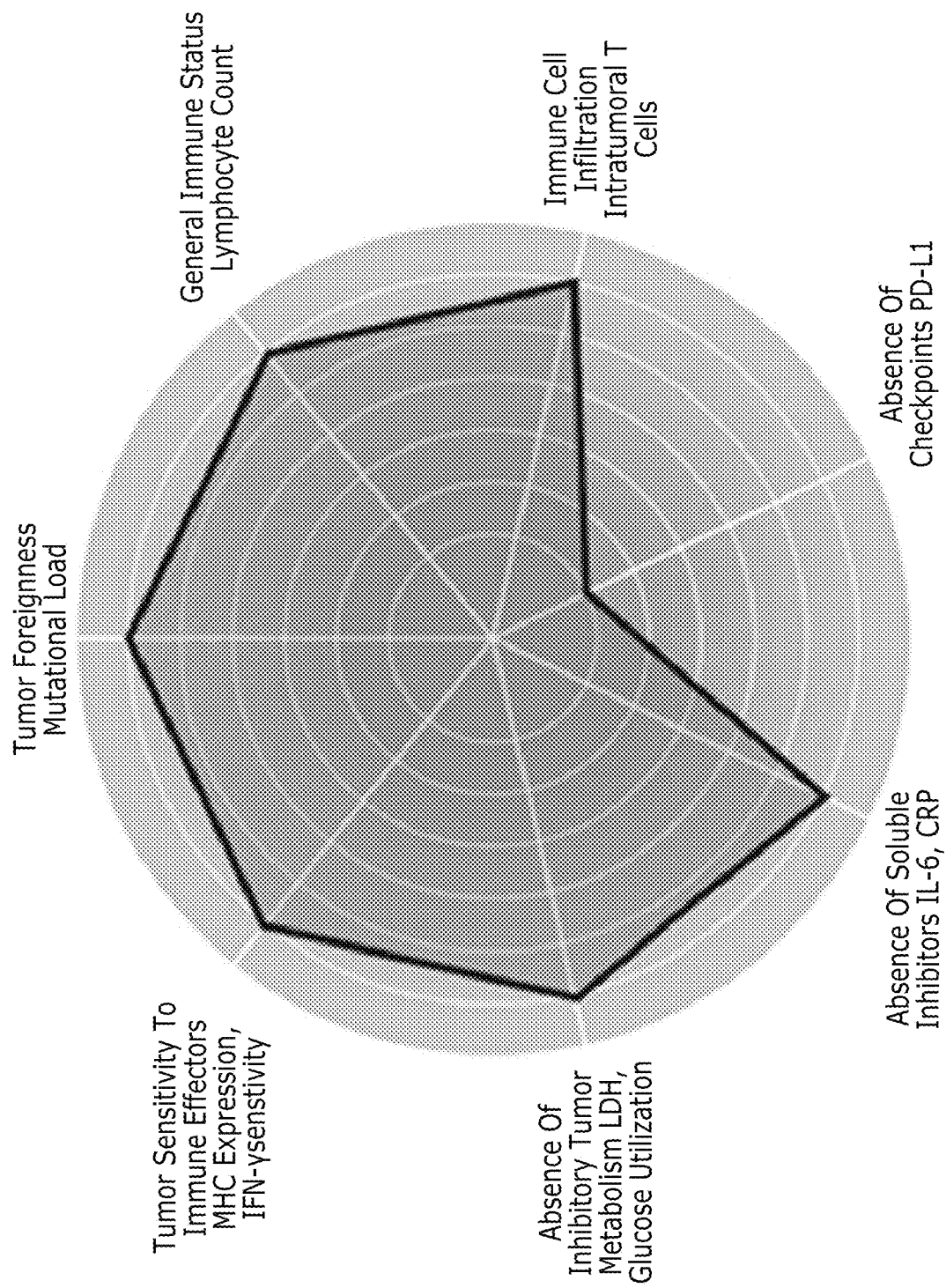
FIG. 3 illustrates an example report in the form of a cancer immunogram score that may be included in a patient report as generated by the process of FIG. 2, in accordance with an example.

FIG. 3 illustrates an example report in the form of a cancer immunogram score that may be included in a patient report. Each spoke represents a scale. In the illustrated example, the scales are foreignness of the tumor, the general immune status, immune cell infiltration, absence of checkpoints, absence of soluble inhibitors, absence of inhibitory tumor metabolism, and tumor sensitivity to immune effectors, each further identified with italicized wording under the scale title representing an example measurement that may be represented by the scale (e.g., mutational load as a measurement of tumor foreignness). On each scale, the score associated with the biological specimen may become a vertex of a polygon, for example, the polygon outlined by a thick black line FIG. 3. The area contained within the polygon may be used as the overall immunotherapy response score (in this example, an immunogram score) for a biological specimen. In an example, the larger values on each scale may be closer to the perimeter of the outer circle and the smaller values may be closer to the centroid of the circle. A larger immunogram score (i.e., larger area of the polygon) may indicate a biological specimen that is more likely to react to immunotherapy. Therefore, the process 222 may be configured to determine any of a plurality of scales, determine a value for each, and determine an overall immunogram score such as by determining a resulting polygonal area. In an example, the larger values on each scale may be closer to the centroid of the circle and the smaller values may be closer to the perimeter of the blue circle. In such examples, a smaller immunogram score (area of the polygon), may indicate a biological specimen that is more likely to react to immunotherapy.

In some examples, the report from process 222 associates an immunotherapy response score with a stored unmarked H&E image. In some examples, the immunotherapy response score is based on immunotherapy associated sequencing data, Immune Cell Infiltration, Immune Gene Expression Signatures, Multiplex PD-L1 and CD8 staining, and/or Multiplex macrophage IHC panels. If the immunotherapy response score contains a plurality of these different features, the immunotherapy response score is considered a multifaceted response score. In particular, multifaceted response scores may be used as scores determined based on imaging features and genetic features. In any case, as exemplified in FIG. 8, the report from process 222 may be a multi-model and multi-biomarker immunogram derived from analyzing received H&E images and associated patient data.

Example 1

As noted above, in various embodiments, selection of the IHC staining protocol may include performing an optimization on the staining protocol. An optimization, as may be performed using the process 208 in FIG. 2, is provided for collecting ground truth annotations for H&E lung tissue models development with chromogenic multiplex IHC.

In this example, the specimen cohort included whole tissue sections of NSCLC (adenocarcinoma) with an equal number of PDL1+ and PDL1– cases (estimated via IHC TC scoring). The cohort included only primary resection specimens with recently-collected samples to avoid any tissue alterations that may affect molecular expressions (e.g., slide age may alter PDL1 expression). In addition to a multiplex slide, i.e., having a multiplex IHC stain, serial sections were extracted from each tissue block to test each antibody in a multiplex panel of antibodies/IHC stains, where the order of each tissue section was logged.

In this example, tissue slides were sectioned in the following order, with two multiplex IHC stain images:

| Order | Section type | Markers |
| --- | --- | --- |
| 1 | Four serial IHC sections | CD3, CD8, CD20, CD68 |
| 2 | H&E | N/A |
| 3 | 7-plex | CD3, CD8, CD20, CD68, CK, PD1, PDL1 |
| 4 | 4-plex | CD3, CD8, CD20, CD68, |
| 5 | 3-plex | CK, PD1, PDL1 |
| 6 | Three serial IHC sections | CK, PD1, PDL1 |

In particular, 11 sections were sliced from each tissue block. The first, second, third, and fourth (the first four sections) were IHC stained. Each of the first four sections had one of the following single-plex IHC targets such that each target is used for one section: CD3, CD8, CD20, or CD68. The fifth section was H&E stained. The sixth section was multiplex IHC stained for seven targets: CD3, CD8, CD20, CD68, CK, PD1, PDL1. The seventh section was multiplexed IHC stained for four targets: CD3, CD8, CD20, CD68. The eighth section was multiplexed IHC stained for three targets: CK, PD1, PDL1. Each of the ninth, tenth, and eleventh sections (the last three sections) were IHC stained. Each of the last three sections had one of the following single-plex IHC targets such that each target is used for one section: CK, PD1, PDL1.

Each antibody in the multiplex IHC staining panel was first optimized individually to define a staining reference library for final staining. In various embodiments, a staining reference is one or more tissue specimens known to have either the presence of the stain antibody's target molecule (positive control tissue) or the absence of the stain antibody's target molecule (negative control tissue). A staining reference library may be commercially available. In one example, the antibody and corresponding staining reference library may be purchased from or provided by the same entity.

The staining reference(s) may be used to determine whether the stain is functioning as expected. For example, stain should be detectable in the positive control tissue after applying the antibody stain to the positive control tissue. Stain should not be detectable in the negative control tissue after applying the antibody stain to the negative control tissue. In one example, if the visible stain in the stained negative control tissue is below an intensity level known in the art and/or if the stain is faintly visible throughout the tissue but not localized, the target molecule may be determined to be absent from the tissue. If the staining references are not stained as expected when the antibody stain is applied to them, then the staining protocol may be adjusted (for example, optimized). Staining references may be used to compare two staining protocols to select a protocol that produces staining that is more accurate, easier to interpret, and/or optimal according to another criterion.

Ways of adjusting a staining protocol are known in the art. For example, an antibody in a stain may be replaced by another antibody having the same target molecule. The chromogen in a stain may be replaced with a different chromogen. The concentration of a stain may be increased or decreased. The amount of time that a stain is in contact with the tissue may be changed. For multiplex staining, each stain may be applied in a certain order relative to the other stains, and the order may be changed.

The staining reference may be used to set thresholds that will be used to determine whether a visibly stained area in a separate tissue specimen (for example, a specimen having an unknown presence/absence status of the target molecule) is determined to be an artifact (indicating the absence of target molecule in that area) or confirmed staining indicating the present of the target molecule. In one example, the threshold is an intensity threshold and the value is higher than the intensity of any stained area in the negative control tissue and lower than the intensity of any stained area in the positive control tissue.

A staining reference tissue specimen may be applicable to multiple antibody stains. For example, a positive control tissue specimen may have more than one class of target molecules present. Similarly, a negative control tissue specimen may have more than one class of target molecules absent. One or more antibody stains targeting the present or absent molecules may be applied to the tissue specimen. After the one or more antibody stains is applied to the staining reference tissue specimen(s), the specimen(s) may be used to set a threshold for any of the applied antibody stains as described above.

examples, the cell type rule is configured to target certain cell types associated with associated data, such as the cancer type, patient information, tissue type, and organ type/biopsy site. Various stainers may be used. In some examples, all tissue sections were stained with a Ventana DISCOVERY ULTRA Research autostainer. Generally, all single-plex IHC slide staining (e.g., the first four and last three slices in this example) are stained following the manufacturer's staining protocols for each antibody using hematoxylin as counterstain.

In some examples, brightfield image capture is used to obtain the histology images. While brightfield image of H&E stained slices may be performed using a DISCOVERY Ultra system using the above antibodies, for IHC stained slices, which may be Immunofluorescent (IF) slides, a modified approach may be used. For example, the specimen may be frozen if specificity/sensitivity is as good for each marker as it is FFPE, since a frozen specimen would allow more tissue and less tissue degradation. In another example, the staining protocol process may calculate for each cell, for each marker, what percent of total stain on the cell is associated with the marker.

In various examples, a multiplexing IHC staining protocol optimization process occurs as follows. At a first step, the staining reference for each antibody in the final multiplex

| Antibody | Cell type | Staining Pattern | Species | Clone | Positive Controls |
|---|---|---|---|---|---|
| CD3 | T cells | Cytoplasm, cell membrane | Rabbit Mono | 2GV6 | Tonsil |
| CD8 | Cytotoxic T lymphocytes | Cell membrane | Rabbit Mono | SP57 | Tonsil |
| CD20 | B lymphocytes | Cell membrane | Mouse Mono | L26 | Tonsil |
| CD68 | Macrophages and some myeloid elements | Cytoplasm, cell membrane | Mouse Mono | KP-1 | Tonsil |
| PanCK | Epithelial cells, occasional stromal staining | Cytoplasm | Mouse Mono | AE1/AE3/PCK26 | Intestine, Liver, Skin |
| PD-1 | T-cells, B-cells, activated monocytes | Cytoplasm | Mouse Mono | NAT105 | Tonsil |
| PD-L1 SP142 | Tumor and immune cells | Cytoplasm, cell membrane | Rabbit Mono | SP142 | Tonsil |

Further in some examples, optimization processes examine the cell type, applying a cell type rule, to identify multiplex combinations to achieve desired combinatorial effects. For example, the optimization process may calculate for each cell, for each marker, what percentage of total stain on the cell is associated with the marker (e.g., calculating the proportions of each stained molecule associated with the individual cell). For example, if a cell has two or more classes of stained molecule (for example, two or more target molecules) associated with it (for example, the stained molecules appear to be located on and/or in the cell), for each class of stained molecule, a ratio, proportion, or percentage (for example, proportion or percentage of total stained molecules associated with the cell) may be calculated. In some examples, the cell type rule is configured to avoid overlapping cell type targets across IHC stains. In some examples, the cell type rule is configured to provide for overlapping of at least some cell type targets. In some examples, the cell type rule is configured to ensure that a threshold number of different cell types are targeted. In some panel is defined. Positive control tissue blocks may be used to test different chromogens and antibody orders. In other examples, chromogens and antibody orders may be stored in a dataset and accessed by the process. For example, chromogens may include 3,3'-Diaminobenzidine (DAB), Red, Teal, Purple, Yellow, Blue, and Silver. One chromogen may be selected for each IHC target. An example antibody chromogen table is as follows:

| Antibody | DAB | Red | Teal | Purple | Yellow | Blue | Silver |
|---|---|---|---|---|---|---|---|
| CD3 | 1 | | | | | | |
| CD8 | | 1 | | | | | |
| CD20 | | | 1 | | | | |
| CD68 | | | | 1 | | | |
| PanCK | | | | | 1 | | |
| PD-1 | | | | | | 1 | |
| PD-L1 | | | | | | | 1 |

In the table, each row represents an antibody class (labeled by the antibody target), and each column represents a chromogen. Ideally, each chromogen should only be conjugated to one antibody class, to make it easier to distinguish distinct antibody classes when two or more antibody classes are combined in an mIHC slide. A number 1 in a cell indicates that the chromogen of that column is conjugated with the antibody class of that row. Ideally, each row and each column should have only one instance of the number 1. Any combination of chromogen and antibody may be used for mIHC staining, especially if the combination satisfies the ideal described in this paragraph.

At a second step, the sequence of chromogens used for protein detection is determined. For example, primary antibodies from different species may be cocktailed for multiplex IHC staining without intermediate destaining, but with sequential detection to avoid any enzymatic deposition. In other examples, primary antibodies from the same species may be used sequentially with DAB counterstain to avoid false colocalization. Denaturing and elution steps will be applied between each sequence to avoid cross-reactivity. For all co-localized markers (e.g., CD3 and CD8), the lowest expressed marker will be applied first. Incubation times for each IHC staining may follow the manufacturer's recommendation for each antibody selected in the panel.

In an example, 50 multiplex IHC slide images (of NSCLC adeno) were used as ground truths to train an machine learning H&E model to detect lymphocytes, macrophages, and tumor cells, and thereby provide a trained machine learning model to derive spatial tumor-immune profiles.

Various modalities may be used to stain and image multiplex stain slices. Virtual multi-staining may be used for whole slide imaging and may include automatically co-registering sections, including IHC stained and scanned serial sections. Typically, 3-way to 5-way multiplex stain slices may be formed and imaged. Multiplex chromogenic IHC provides whole slide imaging and uses simultaneously/sequential application of immunostaining without the removal of previous markers. Typically, 3-way to 5-way multiplex stain slices may be formed and imaged. Multiplexed immunohistochemical consecutive staining on single slide (MICSSS) may be used for whole slide imaging. Typically, up to and including 10-way multiplex stain slices may be formed and imaged. MICSSS uses iterative cycles of immunostaining, scanning, removal of chromogenic enzyme substrate and blocking previous primary antibody. In an example, a multiplex IHC stain may be from a multiplexed chromogenic IHC assay formed using a multiplexed immunohistochemical consecutive staining on single slide (MICSSS) process, e.g., using markers CD8, CD68, CD3, PD1, PDL1, and PanCK. In various implementations, the multiplex IHC staining may comprise multiplex immunofluorescence (IF) used for whole slide imaging or region of interest imaging. Thus references herein to multiplex IHC images include references to multiplex IF images. Multiplex IF staining includes iterative cycles of immunostaining using tyramide signal amplification (TSA) or DNA barcodes. Typically, up to and including 5-8-way multiplex staining can be performed using TSA based staining and up to and including 30-60-way non-TSA based, cycled staining approaches. Example multiplex IF processes included MultiOmyx staining or hyperplexed IF Assay, Tissue-based cycIF, and CODEX. Other example techniques for amplification of the epitope detection, in addition to TSA, include nanocrystal quantum dots, Hapten-based modified multiplexing. MICSSS and multiplex IF processes provide high-throughput multiplex staining and standardized quantitative analysis that allows for fast and efficient ground truth training of a machine learning model.

Figure 4:
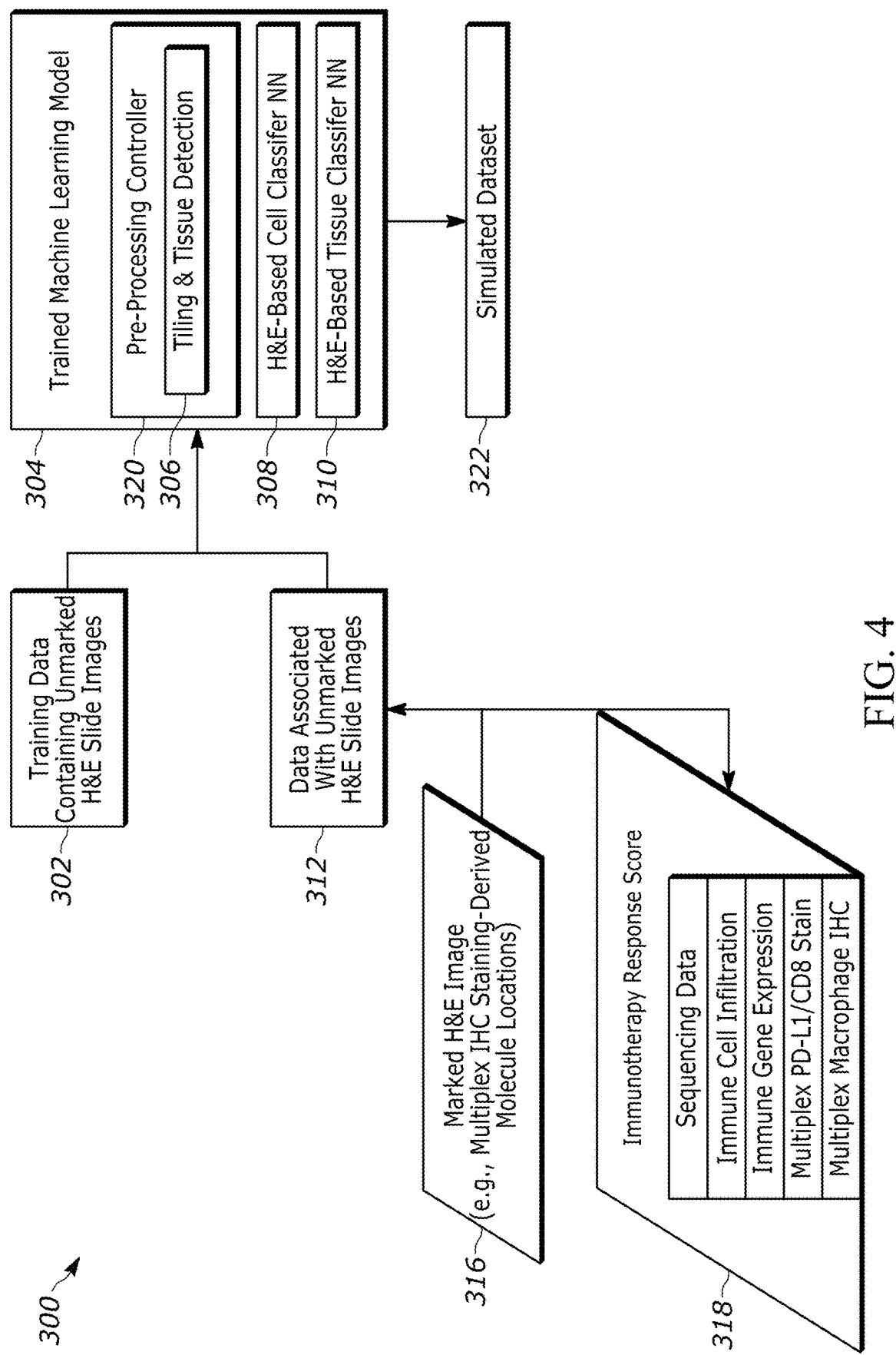
FIG. 4 illustrates a system for generating training data and for training a histology image-based machine learning model, in accordance with an example.

FIG. 4 illustrates a system 300 for generating training data and for training a histology image-based machine learning model. The system 300 may be used to train machine learning model trained for various biomarker determinations, including PD-L1 identification, immune cell type identification (for example, B cell, T cell, CD4 T cell, CD8 T cell), whether the immune cells are located in the tumor region. In accordance with various embodiments herein, the machine learning model is trained to receive histology images, e.g., H&E stained images, and perform tissue classification and cell/molecule classification, for example. Further, the system 300 may be configured to generate an immunotherapy response class based on the number of predicted molecules and/or locations of the predicted molecules. In some implementations, an immunotherapy response class is assigned by comparing the number of predicted molecules to a threshold for each molecule. In some implementations, an immunotherapy response class is assigned by comparing locations of predicted molecules to molecule location criteria. In some examples, the system 300 is configured to predict biomarker status, tumor status, and tumor statistics, based on the tissue and cell/molecule classifications. In some implementations, the immunotherapy response class is one of low, medium, and high lymphocyte infiltration. For example, in some implementations, patients having low tumor infiltration (e.g., low lymphocyte infiltration) could be at higher risk for (i.e., more likely to experience) a progression event while receiving immunotherapy than patients having medium tumor infiltration. The same may be the case for patients having medium tumor infiltration (i.e., more likely to progress) versus patients having high infiltration. Physicians may choose to monitor patients more frequently if they have a higher progression risk (for example, by ordering more frequent imaging—CT scans, MRI, etc.—, ordering genetic testing of either cell-free nucleic acids or cell-associated nucleic acids, or order other follow-up testing).

In various embodiments, in a training mode, The system 300 receives training data in the form of one or more unmarked digital images of a histopathology slide, such as unmarked H&E slide images 302. In some examples, the system 300 creates a high-density, grid-based digital overlay map that identifies the majority class of tissue visible within each grid tile in the digital image. In some examples, the system 300 may generate a digital overlay drawing identifying each cell in a histopathology image, at the resolution level of an individual pixel.

The system 300 includes a machine learning model 304 that, when trained, includes a tiling and tissue detection controller 306, histology image cell/molecule classifier 308, and a histology image tissue classifier 310. In the illustrated example, each of the H&E-based classifiers are neural networks trained to classify received unmarked H&E images, for example, take from a biopsy specimen of a patient.

To affect training of the model 304, the model 304 receives training data containing unmarked H&E slide images 302 and data f14 associated with these unmarked H&E slide images. In various embodiments, the associated data 312 may include marked H&E slide images 316, where such H&E images may be automatically marked to label molecules and locations of molecules derived from multiplex IHC stain images associated with H&E images, in accordance with processes described herein. For example, the marked H&E images 316 may be of slices taken from the same specimen used to generate the slices stained to form the unmarked H&E slide images 302.

In various embodiments, the associated data 312 fed to the machine learning model 304 includes immunotherapy response score data 318 associated with the H&E slide images 302, where that association is based on clinical data. As illustrated, the immunotherapy response score may be of different forms and includes data such as sequencing data, Immune Cell Infiltration, Immune Gene Expression Signatures, Multiplex PD-L1 and CD8 staining, and Multiplex macrophage IHC panels. The immunotherapy response score may be based on a single one of these features or a combination of features resulting in a multifaceted response score, e.g., one based on imaging features and genetic features. Multifaceted response scores may be calculated through various mathematical operators, such as through adding individual response scores, multiplying individual response scores, vectorising individual response scores, etc. and with or without feature dependent weighting factors. Other techniques for determining response scores are described herein and in applications incorporated by reference herein. In yet other embodiments, the associated data 312 may be sequencing data such as tumor mutational burden (TMB), microsatellite Instability (MSI), and T Cell Clonality.

The machine learning model 304 may be part of a deep learning framework to execute processes described in examples herein. The machine learning model 304 includes a pre-processing controller 320 that performs various image processing features. For example, for received unmarked and marked H&E images, the controller 320 may perform aligning/registering of the received images, 302 and 312, such that for each physical location in the biological specimen, pixels associated with that physical location are aligned.

In the illustrated example, the controller 320 includes the tiling & tissue detection controller 306 that performs tiling on the received images, separating each into tiles, where the tiles in any image may be have associated tiles in any other image. In this way, tile level classification and analysis can be performed by the model 304. That is, the cell classifier 308 and the tissue classifier 310 may each be configured as a tile-based neural network classifiers. Not shown, but resulting from the classifiers, the trained machine learning model may include different biomarker classification models, each configured to have a different neural network architecture and to identify a different biomarker in received unmarked H&E images. While in some embodiments the model 304 is configured for training using tile training images, in other architectures the model 304 is configured for training using no tile images, but rather uses whole slide images. Example neural network architecture types for the classifiers 308 and 310 include, ResNet-34, Fully convolutional network (FCN) (FIGS. 6A-6C), Inception-v3, and UNet (see, e.g., FIG. 7). Further still, in some examples, the tiling & tissue detection controller 306 may deploy a neural network trained to performing tiling on received images and trained to perform tissue detection within each tile.

In various embodiments, the pre-processing controller 320 may be a multiple instance learning (MIL) controller configured to separate received images into a plurality of tile images each corresponding to a different portion of the digital image, and the controller 320 uses those tile images in training. Further, in some examples, the controller 320 may use a tile selection process to select between tiles which tiles are to be used for training. In some embodiments, the pre-processing controller 320 is a configured in a feedback configuration that allows for combining a tile section process with a classification model, allowing the tile section process to be informed by a neural network architecture, such as an FCN architecture. In some examples, the tile selection process performed by the controller 320 is a trained MIL process. For example, the machine learning model 304 may generate a simulated dataset 322 during training, where that output is used as an initial input to guide a tile selection process of controller 320.

In various embodiments, the machine learning model 304 is configured with a multi-tile algorithm that concurrently analyzes many tiles in images, both individually and in conjunction with the portion of the image that surrounds each tile. The multi-tile algorithm may achieve a multiscale, multiresolution analysis that captures both the contents of the individual tile and the context of the portion of the image that surrounds the tile. Because the portions of the image that surround two neighboring tiles overlap, analyzing many tiles and their surroundings concurrently instead of separately analyzing each tile with its surroundings reduces computational redundancy and results in greater processing efficiency.

In an example, the machine learning model 304 may store the analysis results in a 3-dimensional probability data array, which contains one 1-dimensional data vector for each analyzed tile. In one example, each data vector contains a list of percentages that sum to 100%, each indicating the probability that each grid tile contains one of the tissue classes analyzed. The position of each data vector in the orthogonal 2-dimensional plane of the data array, with respect to the other vectors, corresponds with the position of the tile associated with that data vector in the digital image, with respect to the other tiles.

In the illustrated example, the pre-processing controller 320 includes the tiling and tissue detection controller 306. In various embodiments, the controller 306 performs tissue detection executes an image tiling process that selects and applies a tiling mask to the received images to parse the images into small sub-images (tiles) for use in training the classifiers 308 and 310. The controller 306 may store a plurality of different tiling masks and select a tiling mask. In some examples, the image tiling process selects one or more tiling masks optimized for different biomarkers, i.e., in some examples, image tiling is biomarker specific. This allows, for example, to have tiles of different pixel sizes and different pixel shapes that are selected specifically to increase accuracy and/or to decrease processing time associated with a particular biomarker. For example, tile sizes optimized for identifying the presence of TILs in an image may be different from tile sizes optimized for identifying PD-L1 or another immunotherapy biomarker. As such, in some examples, the pre-processor controller 320 is configured to perform imaging processing and tiling specific to a type of biomarker, and after the classifiers 308 and 310 analyze images data for that biomarker, the controller 320 may re-process the original image data (e.g., unmarked and marked training H&E images) for analyzing for the next biomarker, and so on, until all biomarkers have been examined for.

Generally speaking, the tiling masks applied by the image tiling process of the controller 306 may be selected to increase efficiency of operation of the machine learning model 304. The tiling mask may be selected based on the size of the received image data, based on the configuration of the machine learning model 304, or some combination thereof.

Tiling masks may vary in the size of tiling blocks. Some tiling masks have uniform tiling blocks, i.e., each the same size. Some tiling masks having tiling blocks of different sizes. The tiling mask applied by the image tiling process may be chosen based on the number of classification layers in the cell classifier 308 and in the tissue classifier 310, for example. In some examples, the tiling mask may be chosen based on the processor configuration of the biomarker prediction system, for example, if the multiple parallel processors are available or if graphical processing units or tensor processing units are used.

In various embodiments, the cell classifier 308 may be configured as a three-class semantic segmentation FCN model developed by modifying a UNet classifier (see, e.g., FIG. 7) replacing a loss function with a cross-entropy function, focal loss function, or mean square error function to form a three-class segmentation model. Three-class nature of the FCN model means that the cell classifier 308 may be configured as a first pixel-level FCN model, that identifies and assigns each pixel of image data into a cell-subunit class: (i) cell interior, (ii) a cell border, or (iii) a cell exterior. This is provided by way of example. The segmentation size of the cell classifier 308 may be determined based on the type of cell to be segmented. For both TILs biomarkers, for example, the cell classifier 308 may be configured to perform lymphocyte identification and segmentation using a three-class FCN model. For example, the cell classifier 308 may be configured to classify pixels in an image as corresponding to the (i) interior, (ii) border, or (iii) exterior of lymphocyte cell. The cell classifier 308 may be configured to identify and segment any number of cells, examples of which include tumor positive, tumor negative, lymphocyte positive, lymphocyte negative, immune cells, including lymphocytes, cytotoxic T cells, B cells, NK cells, macrophages, etc.

The use of a three-class model facilitates, among other things, the counting of each individual cell, especially when two or more cells overlap each other for more accurate classification. Tumor infiltrating lymphocytes will overlap tumor cells. In traditional two-class cell outlining models that only label whether a pixel contains a cell outer edge or not, each clump of two or more overlapping cells would be counted as one cell, which can produce inaccurate results.

In addition to using a three-class model, the cell classifier 308 may be configured to avoid the possibility that a cell that spans two tiles is counted twice, by adding a buffer around all four sides of each tile that is slightly wider than an average cell. The intention is to only count cells that appear in the center, non-buffered region for each tile. In this case, tiles will be placed so that the center, non-buffered region of neighboring tiles are adjacent and non-overlapping. Neighboring tiles will overlap in their respective buffer regions.

In one example, the cell segmentation algorithm of the classifier 308 may be formed of two UNet models. One UNet model may be trained with images of mixed tissue classes, where a human analyst has highlighted the outer edge of each cell and classified each cell according to tissue class. In one example, training data includes digital slide images where every pixel has been labeled as either the interior of a cell, the outer edge of a cell, or the background which is exterior to every cell. In another example, the training data includes digital slide images where every pixel has been labeled with a yes or no to indicate whether it depicts the outer edge of a cell. This UNet model can recognize the outer edges of many types of cells and may classify each cell according to cell shape or its location within a tissue class region assigned by the tissue classifier 310.

Another UNet model may be trained with images of many cells of a single tissue class, or images of a diverse set of cells where cells of only one tissue class are outlined in a binary mask. In one example, the training set is labeled by associating a first value with all pixels showing a cell type of interest and a second value to all other pixels. Visually, an image labeled in this way might appear as a black and white image wherein all pixels showing a tissue class of interest would be white and all other pixels would be black, or vice versa. For example, the images may have only labeled lymphocytes. This UNet model can recognize the outer edges of that particular cell type and assign a label to cells of that type in the digital image of the slide.

The tissue classifier 310 may be configured to classify tissue in a tile as corresponding to one of a number of tissue classes, such as biomarker status, tumor status, tissue type, and/or tumor state/condition, or other information. In an example implementation of a TILs biomarker (an example immunotherapy biomarker), the tissue classifier 310 may classify tissue using tissue classifications, such as Tumor—IHC positive, Tumor—IHC negative, Necrosis, Stroma, Epithelium, or Blood. The tissue classifier 310 may identify boundaries for the different tissue types and generates metadata for use in visually display boundaries and color coding for different tissue types in an overlay mapping report generator.

In various embodiments, the tissue classifier 310 is a tile-based classifier configured to classify tiles as corresponding to one of a plurality of different tissue classifications. Examples of tissue classes include but are not limited to tumor, stroma, normal, lymphocyte, fat, muscle, blood vessel, immune cluster, necrosis, hyperplasia/dysplasia, red blood cells, and tissue classes or cell types that are positive (contain a target molecule of an IHC stain, especially in a quantity larger than a certain threshold) or negative for an IHC stain target molecule (do not contain that molecule or contain a quantity of that molecule lower than a certain threshold). Examples also include tumor positive, tumor negative, lymphocyte positive, and lymphocyte negative.

Figure 6A:
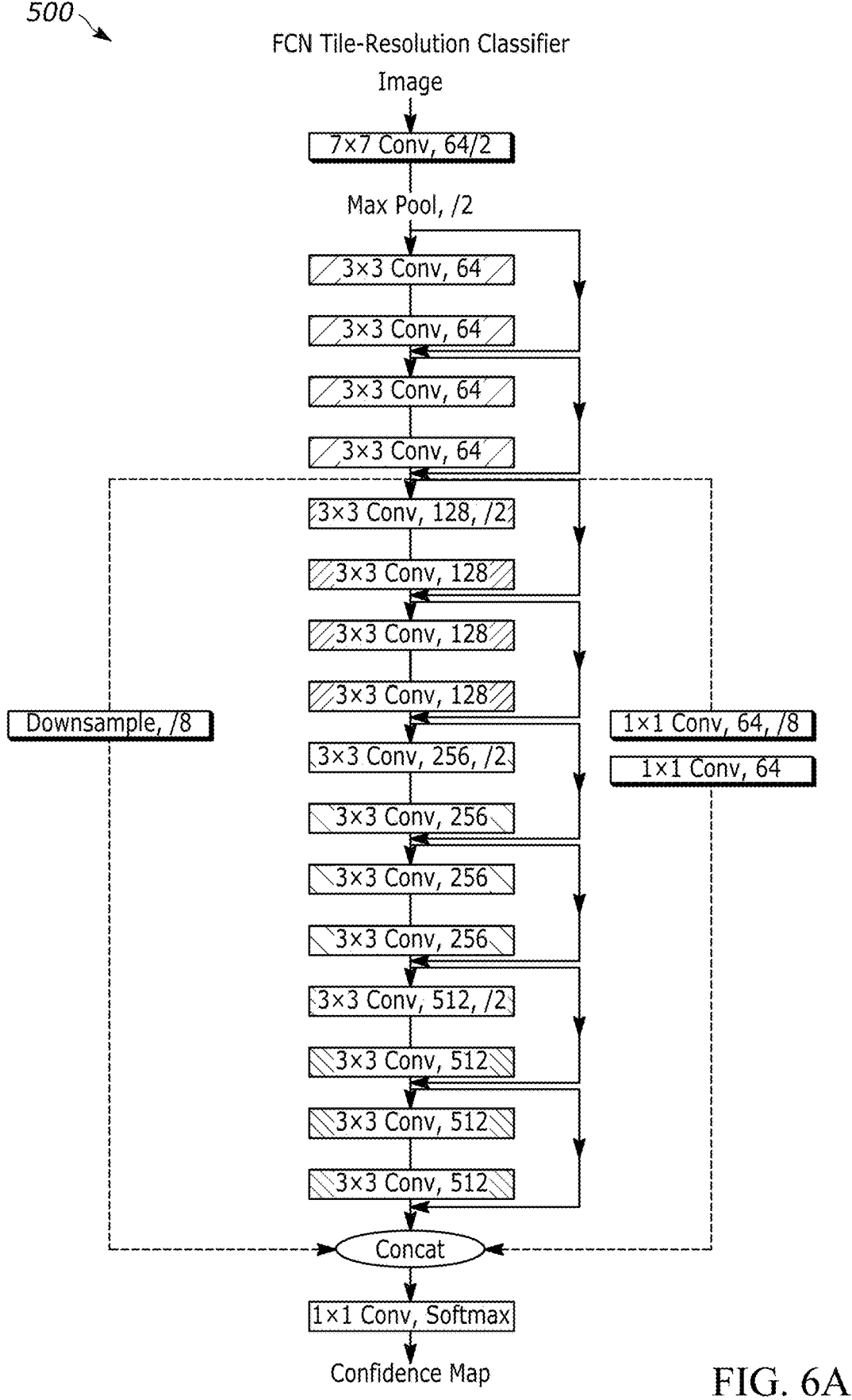
Figure 6C:
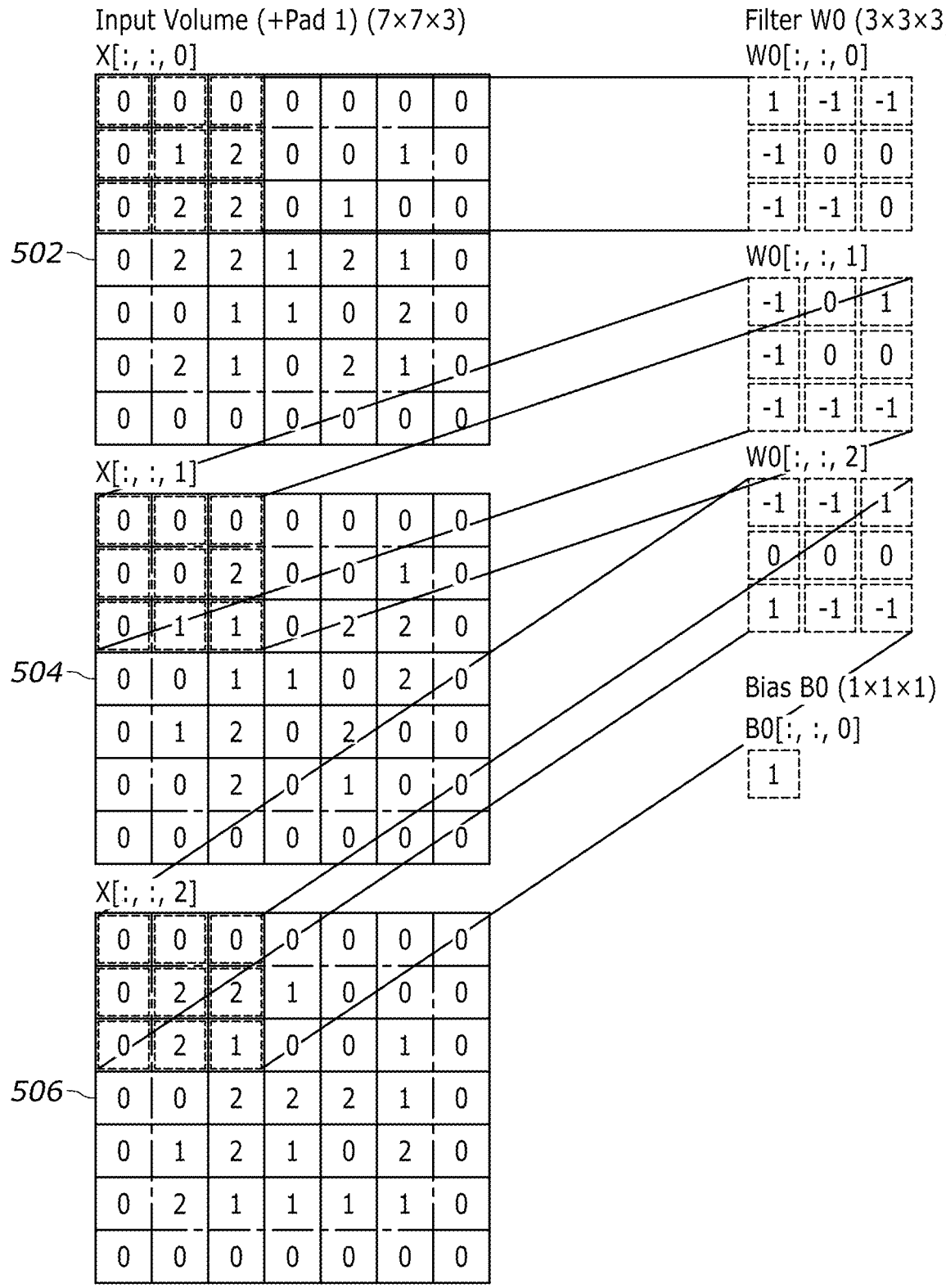

In various embodiments, the tissue classifier 310 is configured as a neural network having an FCN architecture, an example of which is illustrated in FIGS. 6A-6C, and discussed further below.

Figure 7:
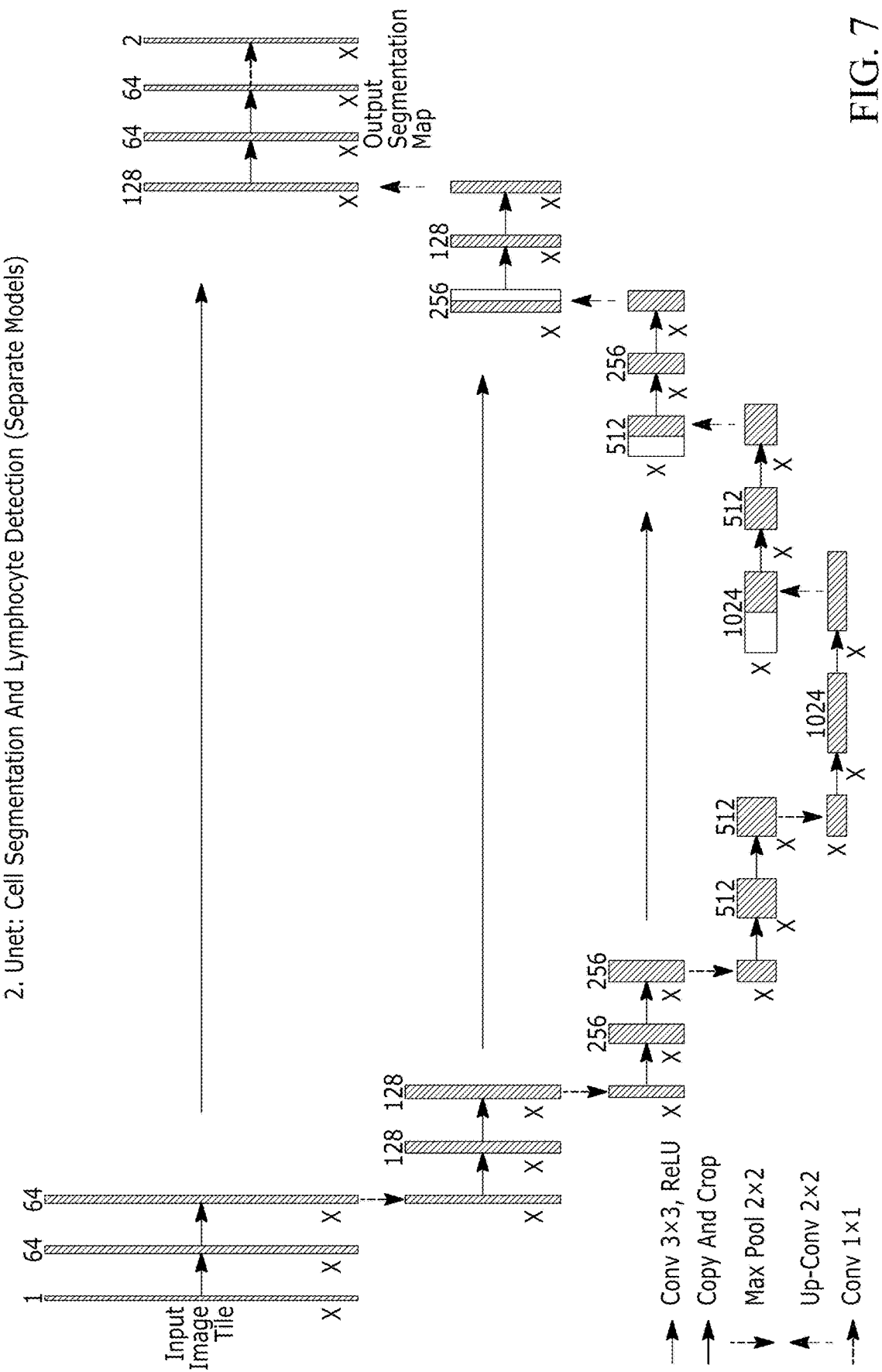
FIG. 7 illustrates an example neural network architecture used for tissue classification and having a UNet architecture, in accordance with an example.

In various embodiments, the cell classifier 308 is configured as a neural network having a UNet architecture, an example of which is illustrated in FIG. 7.

Figure 5:
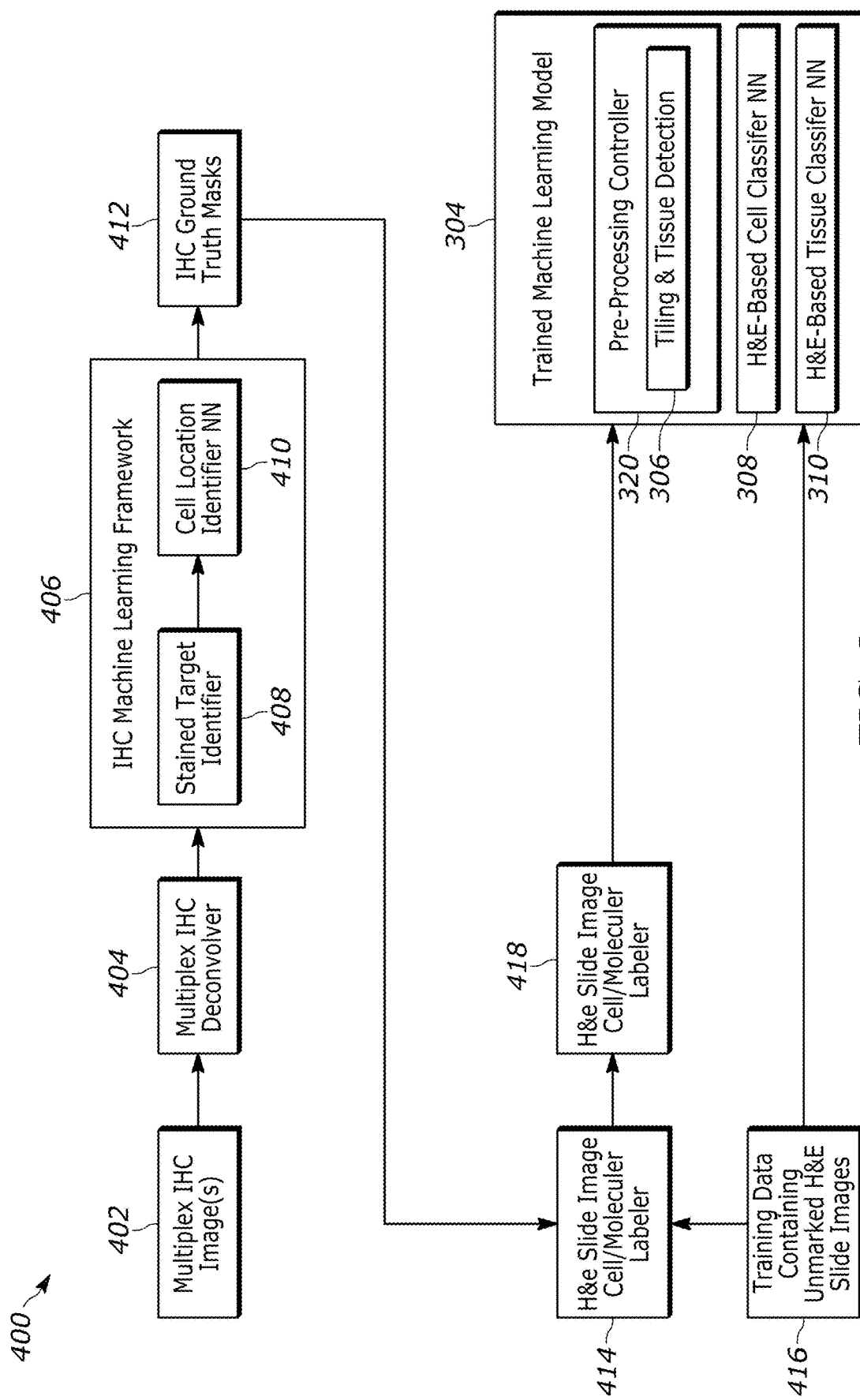
FIG. 5 illustrates an example implementation of a system for generating training data and for training a histology image-based machine learning model, in accordance with an example.

In FIG. 5, example system 400 is provided for generating training data and for training a histology image-based machine learning model, as an example implementation of the system 300 of FIG. 4. Multiplex IHC images 402 are received and provided to a multiplex IHC deconvolver 404. In some examples, an IHC staining process 202 may be used to generate the images 402. In some examples, the images 402 are received from an external image source. For each received multiplex IHC image, the deconvolver 404 detects mixture colors containing more than one IHC stain and identifies the IHC stains that comprise each mixture color, by using a deconvolving process, such as described in 216 of FIG. 2. For example, the deconvolver 404 may determine the location of each IHC stain color by setting an intensity threshold for each stain color and comparing the intensity of the stain color in each pixel to the intensity threshold for that stain color. In some examples, the deconvolver 404 generates an overlay for each IHC stain where each pixel having an intensity that exceeds the threshold for the IHC stain is annotated to indicate presence of the IHC stain in the pixel.

In some examples, the deconvolver 404 generates a plurality of IHC stain specific images for each multiplex IHC image, where those specific images correspond to a different IHC stain. The deconvolver 404 may additionally generate an overlap stain image(s) comprising overlapping IHC stain regions. The output images and image data from the deconvolver is provided to an IHC machine learning framework 406 having a stained target identifier 408 and a cell location identifier 410.

The stained target identifier 408 is configured to examine received IHC images, including single-plex and multiplex IHC images from the deconvolver 404 and determine the location of the associated stained target molecules, targeted by one or more IHC stains forming the multiplex IHC image. Target molecules may be identified in each IHC slide image. In an example implementation, the target molecule in a first tissue layer IHC image is CD3; the target molecule in a second tissue layer IHC image is CD8; the target molecule in a third tissue layer IHC image is CD20; the target molecule in a fourth tissue layer IHC image is CD68; the target molecules in a sixth tissue layer multiplex IHC image are CD3, CD8, CD20, CD68, CK, PD1, and PDL1; the target molecules in a seventh tissue layer multiplex IHC image are CD3, CD8, CD20, and CD68; the target molecules in an eighth tissue layer multiplex IHC image are CK, PD1, and PDL1; the target molecule in a ninth tissue layer IHC image is CK; the target molecule in a tenth tissue layer IHC image is PD1; and the target molecule in an eleventh tissue layer IHC image is PDL1.

In the illustrated example, the cell location identifier 410 is a neural network trained to detect individual cell locations and determines cell type (i.e., inferred cell type). For example, the cell location identifier 410 may detect which individual cells are lymphocytes in the multiplex IHC image(s) and determine their locations. The cell location identifier 410 may be configured in a UNET neural network, such as having the configuration like that illustrated in FIG. 7.

The machine learning framework 406 annotates the IHC images, single-plex and multiplex images, with the identified target molecules and identified cell locations and cell types (i.e., inferred cell types) and provides these as IHC ground truth mask images 412. For training the machine learning model 404, these ground truth masks 412 are provided to an H&E slide labeler 414. The labeler 414 performs alignment and/or registration of the ground truth masks 412 to received unmarked H&E slide images 416, for example, such that for each physical location in the biological specimen, all pixels associated with that physical location are aligned. The labeler 414 marks the location on the unmarked H&E image that corresponds to the locations of the target molecules stained on the IHC ground truth masks 412, thereby generating one or more marked H&E slide images 418. In various embodiments, for each cell in the H&E image having a location that corresponds to the location of one of the IHC ground truth mask images 412, the labeler 414 may calculate the percentage of stained pixels overlapping the cell that is associated with each IHC stain to determine an IHC stain profile for each cell and store the same as image data of the marked H& slide image.

In marked H&E slide images 418 and the unmarked H&E slide images 416 are provided to the machine learning model 304 for training the classifiers 308 and 310, in accordance with techniques described herein.

Figure 8:
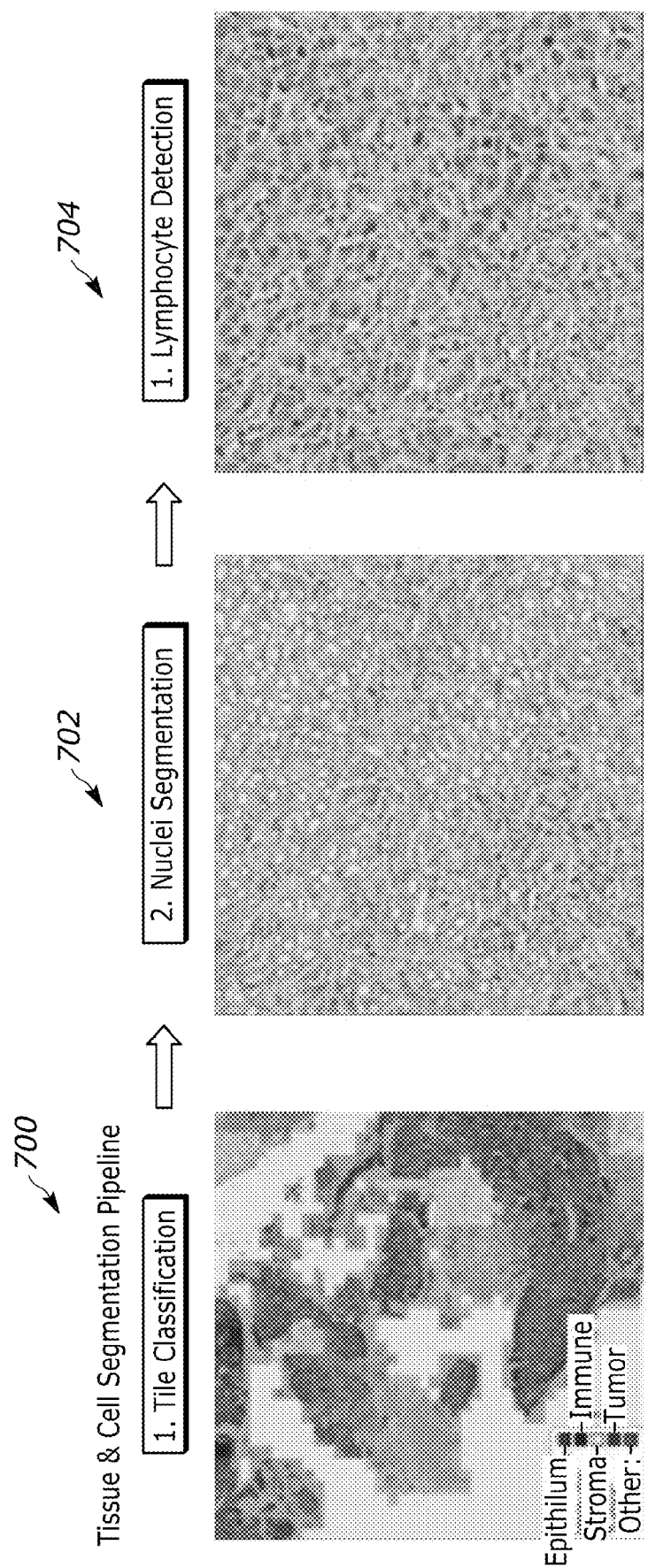
FIG. 8 illustrates example H&E images at different stages of processing by a prediction system, in accordance with an example.
Figure 9:
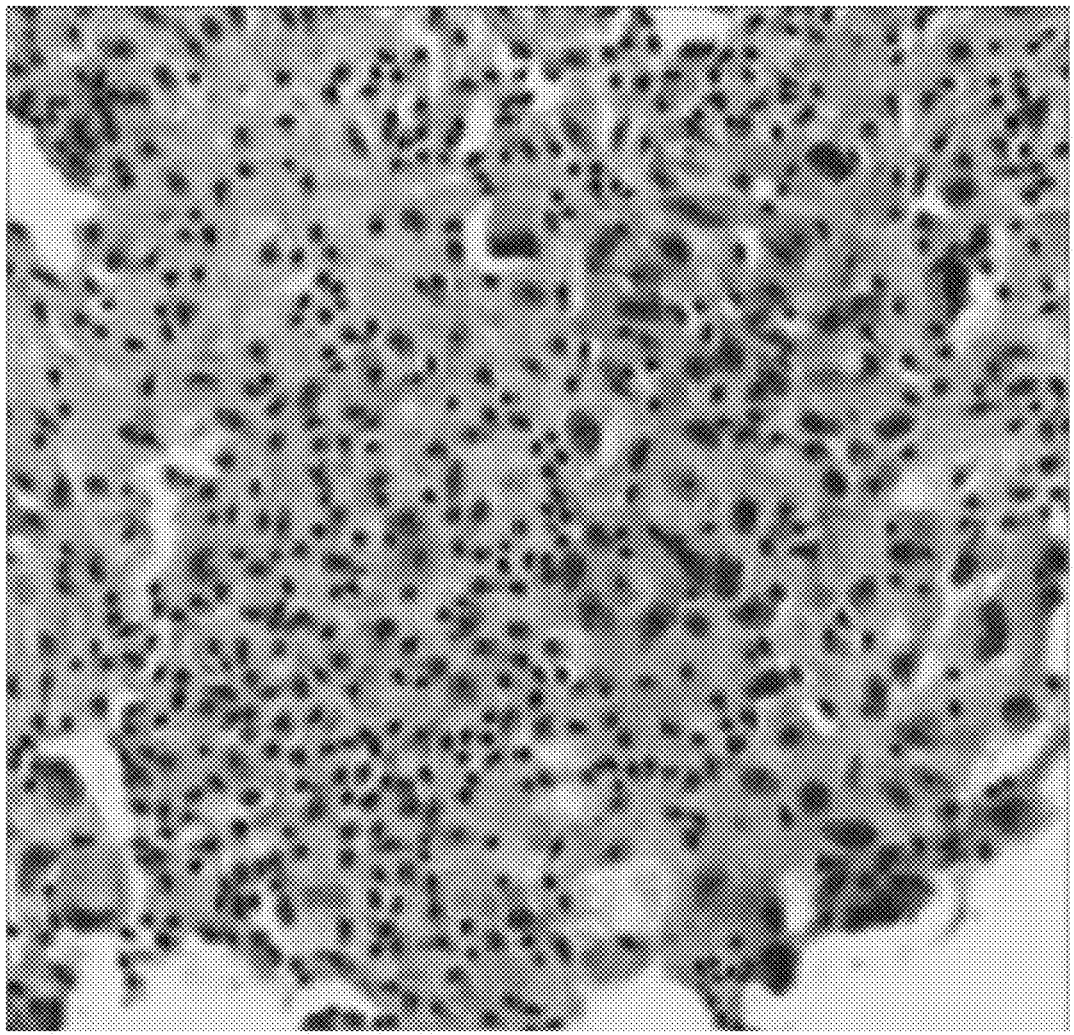
FIG. 9 illustrates an example H&E image resulting from a prediction system and showing lymphocyte cells detected within tumor tiles (TILs) determined by the prediction system, in accordance with an example.

FIG. 8 illustrates example images of H&E images at different stages of processing, in an example implementation. An H&E image 700 has been separated into tiles and each tile classified by a tissue classification process, identifying the tile as corresponding to one of plurality of different tissue types: epithelium, immune, stroma, tumor, or other. The classified tiles may then be each provided to a cell classifier. Or, in some examples, only certain classified tiles are provided for cell classification, such as tiles classified as corresponding to tumor tissue. Multiple instance learning models may be used in a tile classifier to extract only tumor tiles, for example. Image 702 is an example tile after a cell classifier has identified nuclei within the tile and performed a nuclei segmentation highlight the nuclei. Image 704 is an example tile after the cell classifier has performed the cell segmentation and then performs a cell detection to identify, in this example, lymphocyte cells and their locations in the tile. This process is repeated across all tiles forming the H&E image 700 or across a subset of the tiles thereof, such as the tumor classified tiles. From there, the machine learning model may derive various statistics. Example statistics include a "TIL score" for the image, that is, from count of all lymphocyte cells detected within tumor tiles (see, FIG. 9). Estimated tumor percentage, that is, a ratio of all tiles classified as tumor over total tissue tiles, is another statistic. Other additional statistics include whole image-level cell counts (mean, standard deviation, quartiles, etc.). Cell morphology features may be determined, such as texture-based features derived from the detected cells. Fractals and tumor nuclei morphology may be determined using Delaunay triangulation (w/o normalization) techniques, for example. These and other statistics may be calculated by a tumor report generator, such as report generator 180, or other processor or process. In implementations, various statistics can be calculated from the output of the trained machine learning models, including one or more of percentage of cells having a particular molecule, percentage of cells having a particular ratio of molecules, location relationships among cell types, extent of mixing of cell types, and degree of tumor infiltration by lymphocytes. Such statistics may be determined from classification data, in particular, from the number of predicted molecules and locations of the predicted molecules contained in the classification data. In some implementations, these statistics are determined by a machine learning model, such as machine learning model 304. In any event, any of such data may be provided to a pathologist in an automatically generated report. From these labeled H&E images and developed statistics, H&E derived features may be determined, such as assigning an immunotherapy response class. Examples include predicting immunotherapy response outcome for patients identified with NSCLC, predicting colorectal cancer and lung metastasis. These may be presented to a pathologist in a generated report.

FIG. 6A illustrates an example neural network architecture 500 that may be used for tissue classification, such as that performed by tissue classifier 310 in FIG. 4 and/or process 216 in FIG. 2. In particular, the architecture 500 has a tile-resolution FCN configuration. As shown, the tile-resolution FCN configuration included in the tissue classifier 310 has additional layers of 1×1 convolution in a skip connection, downsampling by a factor of 8 in a skip connection, and a confidence map layer, and replaces an average pooling layer with a concatenation layer, and a fully connected FCN layer with a 1×1 convolution and Softmax layer. The added layers convert a classification task into a classification-segmentation task. This means that instead of receiving and classifying a whole image as one tissue class label, the added layers allow the tile-resolution FCN to classify each small tile in the user-defined grid as a tissue class.

These added and replacement layers convert a CNN to a tile-resolution FCN without requiring the upsampling performed in the later layers of traditional pixel-resolution FCNs. Upsampling is a method by which a new version of an original image can be created with a higher resolution value than the original image. However, upsampling is a time-consuming, computation-intense process, which can be avoided with the present architecture. FIG. 6B illustrates example output sizes for different layers and resulting sublayers of the architecture 500.

There are many methods known in the art for upsampling, including nearest-neighbor, bilinear, hermite, bell, Mitchell, bicubic, and Lanczos resampling. In one example, 2× upsampling means that a pixel with red green blue (RGB) values will be split into four pixels, and the RGB values for the three new pixels may be selected to match the RGB values of the original pixel. In another example, the RGB values for the three new pixels may be selected as the average of the RGB values from the original pixel and the pixels that are adjacent to the neighboring pixel.

Because the RGB values of the new pixels may not accurately reflect the visible tissue in the original slide that was captured by the digital slide image, upsampling can introduce errors into the final image.

In an example, instead of labeling individual pixels, the tile-resolution FCN architecture 500 is programmed to analyze a large square tile made of small square tiles, producing a 3D array of values that each represent the probability that one tissue class classification label matches the tissue class depicted in each small tile. A convolution layer performs the multiplication of at least one input image matrix by at least one filter matrix. In the first convolution later, the input image matrix has a value for every pixel in the large square tile input image, representing visual data in that pixel (for example, a value between 0 and 255 for each channel of RGB).

The filter matrix may have dimensions selected by the user, and may contain weight values selected by the user or determined by backpropagation during CNN model training. In one example, in the first convolution layer, the filter matrix dimensions are 7×7 and there are 64 filters. The filter matrix may represent visual patterns that can distinguish one tissue class from another.

In an example where RGB values populate the input image matrix, the input image matrix and the filter matrices will be 3-dimensional. Each filter matrix is multiplied by each input image matrix to produce a result matrix. All result matrices produced by the filters in one convolution layer may be stacked to create a 3-dimensional result matrix having dimensions such as rows, columns, and depth. The last dimension, depth, in the 3-D result matrix will have a depth equal to the number of filter matrices. The resulting matrix from one convolution layer becomes the input image matrix for the next convolution layer.

A convolution layer title that includes "/n", where n is a number, indicates that there is a downsampling (also known as pooling) of the result matrix produced by that layer. The n indicates the factor by which the downsampling occurs. Downsampling by a factor of 2 means that a downsampled result matrix with half as many rows and half as many columns as the original result matrix will be created by replacing a square of four values in the result matrix by one of those values or a statistic calculated from those values. For example, the minimum, maximum, or average of the values may replace the original values.

The architecture 500 also adds skip connections (shown in FIG. 6A as black lines with arrows that connect convolution layers directly to the concatenation layer). The skip connection on the left includes downsampling by a factor of 8, and the skip connection on the right includes two convolution layers that multiply an input image matrix by filter matrices that each have dimensions of 1×1. Because of the 1×1 dimensions of the filter matrices in these layers, only an individual small square tile contributes to its corresponding probability vector in the result matrices created by the purple convolution layers. These result matrices represent a small focus of view.

In all of the other convolution layers, the larger dimensions of the filter matrices allow the pixels in each medium square tile, including the small square tile at the center of the medium square tile, to contribute to the probability vector in the result matrix that corresponds with that small square tile. These result matrices allow the contextual pixel data patterns surrounding the small square tile to influence the probability that each tissue class label applies to the small square tile. These result matrices represent a large focus of view.

The 1×1 convolution layers in the skip connection allow the algorithm to regard the pixel data patterns in the center small square tile as either more or less important than pixel data patterns in the rest of the surrounding medium square tile. The amount of importance is reflected by the weights that the trained model multiplies by the final result matrix from the skip connection layers (shown on the right side of FIG. 6A) compared to the weights that the trained model multiplies by the final result matrix from the medium tile convolution layers during the concatenation layer.

The downsampling skip connection shown on the left side of FIG. 6A creates a result matrix with a depth of 64. The 3×3 convolution layer having 512 filter matrices creates a result matrix with a depth of 512. The 1×1 convolution layer having 64 filter matrices creates a result matrix with a depth of 64. All three of these results matrices will have the same number of rows and the same number of columns. The concatenation layer concatenates these three results matrices to form a final result matrix with the same number of rows and the same number of columns as the three concatenated matrices, and a depth of 64+512+64 (640). This final result matrix combines the large and small focus of view matrices.

The final result matrix may be flattened to 2 dimensions by multiplying a factor by every entry, and summing the products along each depth. Each factor may be selected by the user, or may be selected during model training by backpropagation. Flattening will not change the number of rows and columns of the final results matrix, but will change the depth to 1.

The 1×1 convolution layer receives the final result matrix and filters it with one or more filter matrices. The 1×1 convolution layer may include one filter matrix associated with each tissue class label in the trained algorithm. This convolution layer produces a 3-D result matrix that has a depth equal to the number of tissue class labels. Each depth corresponds to one filter matrix and along the depth of the result matrix there may be a probabilities vector for each small square tile. This 3-D result matrix is the 3-dimensional probability data array, and the 1×1 convolution layer stores this 3-D probability data array.

A Softmax layer may create a 2-dimensional probability matrix from the 3-D probability data array by comparing every value in each probabilities vector and selecting the tissue class associated with the maximum value to assign that tissue class to the small square tile associated with that probabilities vector.

The stored 3-dimensional probability data array or the 2-D probability matrix may then be converted to a tissue class overlay map in the final confidence map layer, to efficiently assign a tissue class label to each tile.

In one example, to counteract shrinkage, input image matrices have added rows and columns on all four outer edges of the matrices, wherein each value entry in the added rows and columns is a zero. These rows and columns are referred to as padding. In this case, the training data input matrices will have the same number of added rows and columns with value entries equal to zero. A difference in the number of padding rows or columns in the training data input matrices would result in values in the filter matrices that do not cause the tissue class locator 216 to accurately label input images.

In the FCN shown in FIG. 6A, 217 total outer rows or columns on each side of the input image matrix will be lost to shrinkage before the skip connection, due to the gray and blue layers. Only the pixels located in the small square tiles will have a corresponding vector in the result matrices created by the green layers and beyond.

In one example, each medium square tile is not padded by adding rows and columns with value entries of zero around the input image matrix that corresponds to each medium square tile because the zeroes would replace image data values from neighboring medium square tiles that the tissue class locator 216 needs to analyze. In this case, the training data input matrices will not be padded either.

FIG. 6C is a visualization of each depth of an exemplary 3-dimensional input image matrix being convoluted by two exemplary 3-dimensional filter matrices. In an example where an input image matrix contains RGB channels for each medium square tile, the input image matrix and filter matrices will be 3-dimensional. In one of the three dimensions, the input image matrix and each filter matrix will have three depths, one for red channel, one for green channel, and one for blue channel.

The red channel (first depth) 502 of the input image matrix is multiplied by the corresponding first depth of the first filter matrix. The green channel (second depth) 504 is multiplied in a similar fashion, and so on with the blue channel (third depth) 506. Then, the red, green, and blue product matrices are summed to create a first depth of the 3-dimensional result matrix. This repeats for each filter matrix, to create an additional depth of the 3-dimensional result matrix that corresponds to each filter.

Figure 10:
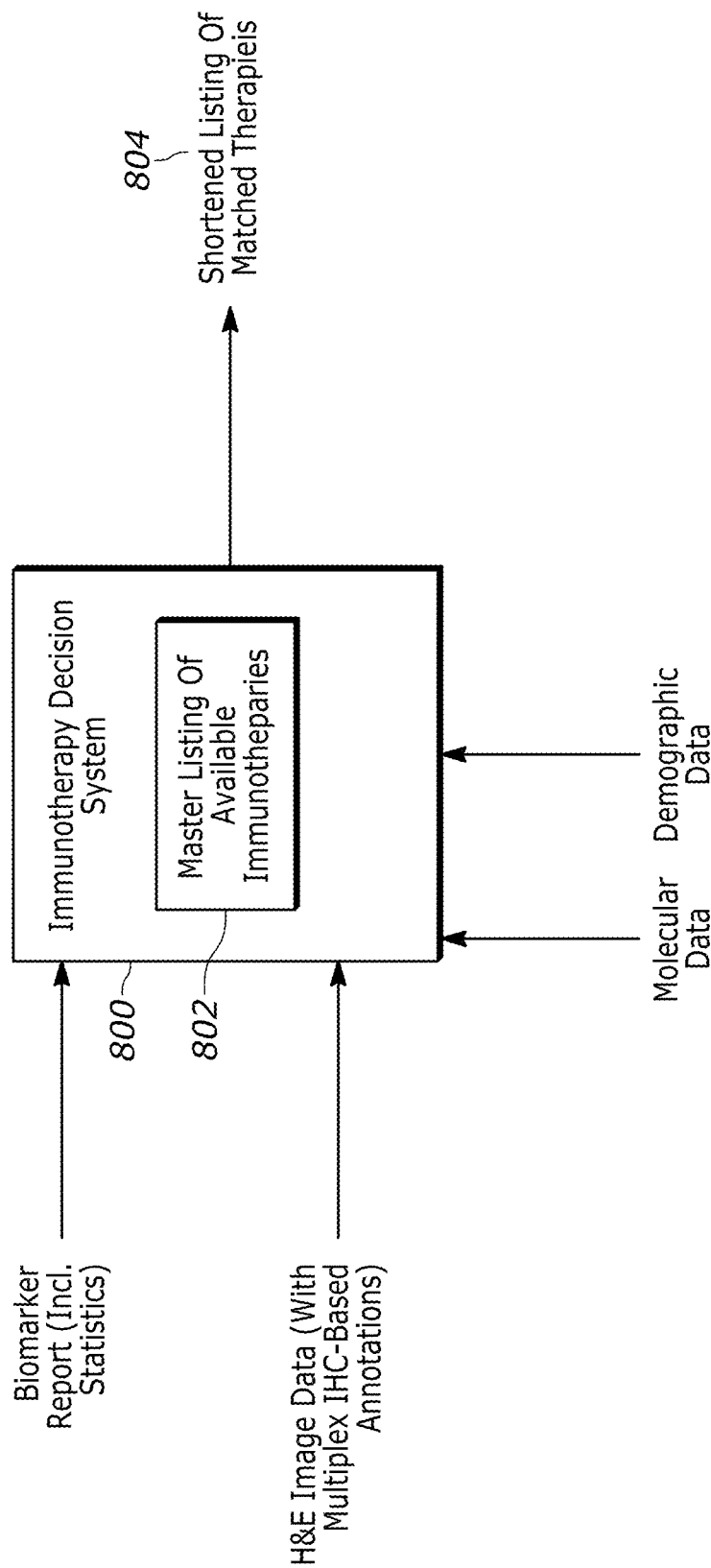
FIG. 10 illustrates an immunotherapy response decision system capable of determining a listing of possible immunotherapies based on received data, in accordance with an example.

As shown in FIG. 10, the output from the trained machine learning model 304 may be provided to a immunotherapy response decision system 800 (such as may be part of a genomic sequencing system, oncology system, chemotherapy decision system, immunotherapy decision system, or other therapy decision system) that determines a listing of possible immunotherapies based on received data, i.e., the H&E image(s) with tissue and cell/molecule classifications biomarker reports, such as statistics including those based on the biomarker metrics, genomic sequencing data, etc. and other statistics determined by the machine learning model 304. The system 800 analyzes the classification information and or statistics and other received molecular data against available immunotherapies 802, and the system 800 recommends a matched listing of possible tumor-type specific immunotherapies 804, filtered from the list of available immunotherapies 802, in the form of a matched therapy report. In some examples, the listing of immunotherapies is ranked in an order as determined by the decision system 800, for example, a ranked order based on predicted likelihood of success among the matched listing of possible immunotherapies.

Figure 11:
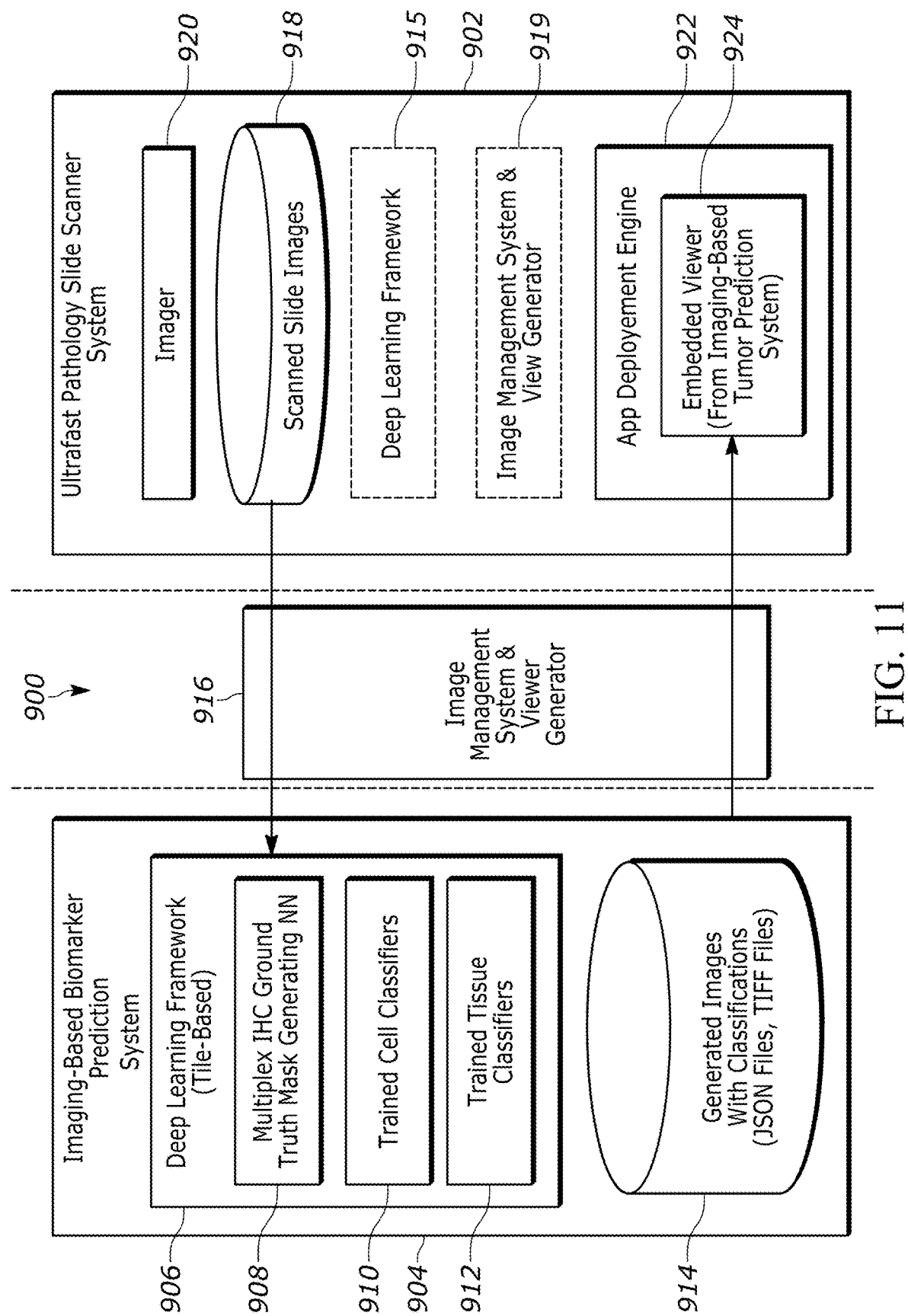
FIG. 11 illustrates an example system having a dedicated ultrafast pathology (slide) scanner system and an imaging-based biomarker prediction system, in accordance with an example.

In various examples, the techniques herein may be deployed partially or wholly within a dedicated slide imager, such as a high throughput digital scanner. FIG. 11 illustrates an example system 900 having a dedicated ultrafast pathology (slide) scanner system 902, such as a Philips IntelliSite Pathology Solution available from Koninklijke Philips N. V. of Amsterdam, Netherlands. In some examples, the pathology scanner system 902 may contain a plurality of trained biomarker classification models. Exemplary models may include, for instance, those disclosed in U.S. application Ser. No. 16/412,362. The scanner system 902 is coupled to an imaging-based biomarker prediction system 904, implementing processes as discussed and illustrated in examples herein. For example, in the illustrated example, the system 904 includes a deep learning framework 906 based on tile-based classification modules, in accordance with examples herein, having multiplex IHC image ground truth mask generating neural network 908, a trained cell classifier 910 and a trained tissue classifier 912. Through the NN 908, the deep learning framework 906 generates ground truth masks from multiplex IHC images where those masks are used to train the cell classifier 910 and tissue classifiers 912. The deep learning framework 906 performs biomarker and tumor classifications on histopathology images, e.g., unmarked H&E slide images, and stores the classification data as overlay data with the original images in a generated images database 914. The images may be saved as TIFF files, for example. Although the database 914 may include JSON files and other data generated by the classification processes herein. In some examples, the deep learning framework may be integrated in whole or in part within the scanner 902, as shown in optional block 915.

To manage generated images, which can be quite large, an image management system and viewer generator 916 is provided. In the illustrated example, the system 916 is illustrated as external to the imaging-based biomarker prediction system 904, connected by a private or public network. Yet, in other examples, all or part of the system 916 may be deployed in the system 904, as shown at 919. In some examples, the system 916 is cloud based, and stores generated images from (or instead of) the database 0914. In some examples, the system 3016 generates a web-accessible cloud based viewer, allowing pathologists to access, view, and manipulate, through a graphic user interface, histopathology images with various classification overlays.

In some examples, the image management system 916 manages receipt of scanned slide images 918 from the scanner 902, where these slide images are generated from an imager 920.

In the illustrated example, the image management system 916 generates an executable viewer App 924 and deploys that App 924 to an App Deployment Engine 922 of the scanner 902. The App Deployment Engine 922 may provide functionality such as GUI generation allowing users to interact with the view App 924, an App marketplace allowing users to download the viewer App 924 from the image management system 916 or from other network accessible sources.

FIG. 12 illustrates an example computing device 1000 for implementing the imaging-based biomarker prediction system 100 of FIG. 1. As illustrated, the system 100 may be implemented on the computing device 1000 and in particular on one or more processing units 1010, which may represent Central Processing Units (CPUs), and/or on one or more Graphical Processing Units (GPUs) 1011, including clusters of CPUs and/or GPUs, and/or one or more tensor processing unites (TPU) (also labeled 1011), any of which may be cloud based. Features and functions described for the system 100 may be stored on and implemented from one or more non-transitory computer-readable media 1012 of the computing device 1000. The computer-readable media 1012 may include, for example, an operating system 1014 and the deep learning framework 1016 having elements corresponding to that of machine learning model 304, deep learning framework 906 and deep learning framework 915, including the pre-processing controllers and classifies therein. More generally, the computer-readable media 1012 may store trained deep learning models, executable code, etc. used for implementing the techniques herein. The computer-readable media 1012 and the processing units 1010 and TPU(S)/GPU(S) 1011 may store histology images and data, tissue classification data, cell segmentation data, lymphocyte segmentation data, TILs metrics, and other data herein in one or more databases 1013. The computing device 1000 includes a network interface 1024 communicatively coupled to the network 1050, for communicating to and/or from a portable personal computer, smart phone, electronic document, tablet, and/or desktop personal computer, or other computing devices. The computing device further includes an I/O interface 1026 connected to devices, such as digital displays 1028, user input devices 1030, etc. In some examples, as described herein, the computing device 1000 generates biomarker prediction as an electronic document 1015 that can be accessed and/or shared on the network 1050. In the illustrated example, the system 100 is implemented on a single server 1000. However, the functions of the system 100 may be implemented across distributed devices 1000, 1002, 1004, etc. connected to one another through a communication link. In other examples, functionality of the system 100 may be distributed across any number of devices, including the portable personal computer, smart phone, electronic document, tablet, and desktop personal computer devices shown. In other examples, the functions of the system 100 may be cloud based, such as, for example one or more connected cloud TPU (s) customized to perform machine learning processes. The network 1050 may be a public network such as the Internet, private network such as research institution's or corporation's private network, or any combination thereof. Networks can include, local area network (LAN), wide area network (WAN), cellular, satellite, or other network infrastructure, whether wireless or wired. The network can utilize communications protocols, including packet-based and/or datagram-based protocols such as internet protocol (IP), transmission control protocol (TCP), user datagram protocol (UDP), or other types of protocols. Moreover, the network can include a number of devices that facilitate network communications and/or form a hardware basis for the networks, such as switches, routers, gateways, access points (such as a wireless access point as shown), firewalls, base stations, repeaters, backbone devices, etc.

The computer-readable media may include executable computer-readable code stored thereon for programming a computer (e.g., comprising a processor(s) and GPU(s)) to the techniques herein. Examples of such computer-readable storage media include a hard disk, a CD-ROM, digital versatile disks (DVDs), an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. More generally, the processing units of the computing device 1300 may represent a CPU-type processing unit, a GPU-type processing unit, a TPU-type processing unit, a field-programmable gate array (FPGA), another class of digital signal processor (DSP), or other hardware logic components that can be driven by a CPU.

It is noted that while example deep learning frameworks and neural networks herein have been described as configured with example machine learning architectures (FCN configurations and UNET configurations), any number of suitable convolutional neural network architectures may be used. Broadly speaking, the deep learning frameworks herein may implement any suitable statistical model (e.g., a neural network or other model implemented through a machine learning process) that will be applied to each of the received images. As discussed herein, that statistical model may be implemented in a variety of manners. In some examples, machine learning is used to evaluate training images and develop classifiers that correlate predetermined image features to specific categories of TILs status. In some examples, image features can be identified as training classifiers using a learning algorithm such as Neural Network, Support Vector Machine (SVM) or other machine learning process. Once classifiers within the statistical model are adequately trained with a series of training images, the statistical model may be employed in real time to analyze subsequent images provided as input to the statistical model for predicting biomarker status. In some examples, when a statistical model is implemented using a neural network, the neural network may be configured in a variety of ways. In some examples, the neural network may be a deep neural network and/or a convolutional neural network. In some examples, the neural network can be a distributed and scalable neural network. The neural network may be customized in a variety of manners, including providing a specific top layer such as but not limited to a logistics regression top layer. A convolutional neural network can be considered as a neural network that contains sets of nodes with tied parameters. A deep convolutional neural network can be considered as having a stacked structure with a plurality of layers. The neural network or other machine learning processes may include many different sizes, numbers of layers and levels of connectedness. Some layers can correspond to stacked convolutional layers (optionally followed by contrast normalization and max-pooling) followed by one or more fully-connected layers. For neural networks trained by large datasets, the number of layers and layer size can be increased by using dropout to address the potential problem of overfitting. In some instances, a neural network can be designed to forego the use of fully connected upper layers at the top of the network. By forcing the network to go through dimensionality reduction in middle layers, a neural network model can be designed that is quite deep, while dramatically reducing the number of learned parameters.

Thus, as provided, a system for performing the methods described herein may include a computing device, and more particularly may be implemented on one or more processing units, for example, Central Processing Units (CPUs), and/or on one or more or Graphical Processing Units (GPUs), including clusters of CPUs and/or GPUs. Features and functions described may be stored on and implemented from one or more non-transitory computer-readable media of the computing device. The computer-readable media may include, for example, an operating system and software modules, or "engines," that implement the methods described herein. More generally, the computer-readable media may store batch normalization process instructions for the engines for implementing the techniques herein. The computing device may be a distributed computing system, such as an Amazon Web Services cloud computing solution.

The functions of the engines may be implemented across distributed computing devices, etc. connected to one another through a communication link. In other examples, functionality of the system may be distributed across any number of devices, including the portable personal computer, smart phone, electronic document, tablet, and desktop personal computer devices shown. The computing device may be communicatively coupled to the network and another network. The networks may be public networks such as the Internet, a private network such as that of a research institution or a corporation, or any combination thereof. Networks can include, local area network (LAN), wide area network (WAN), cellular, satellite, or other network infrastructure, whether wireless or wired. The networks can utilize communications protocols, including packet-based and/or datagram-based protocols such as Internet protocol (IP), transmission control protocol (TCP), user datagram protocol (UDP), or other types of protocols. Moreover, the networks can include a number of devices that facilitate network communications and/or form a hardware basis for the networks, such as switches, routers, gateways, access points (such as a wireless access point as shown), firewalls, base stations, repeaters, backbone devices, etc.

The methods and systems described above may be utilized in combination with or as part of a digital and laboratory health care platform that is generally targeted to medical care and research. It should be understood that many uses of the methods and systems described above, in combination with such a platform, are possible. One example of such a platform is described in U.S. Patent Publication No. 2021/0090694, titled "Data Based Cancer Research and Treatment Systems and Methods", and published Mar. 25, 2021, which is incorporated herein by reference and in its entirety for any and all purposes.

For example, an implementation of one or more embodiments of the methods and systems as described above may include microservices constituting a digital and laboratory health care platform supporting immunotherapy response prediction from H&E images. Embodiments may include a single microservice for executing and delivering immunotherapy response prediction or may include a plurality of microservices each having a particular role which together implement one or more of the embodiments above. In one example, a first microservice may execute H&E image analysis and molecule location prediction in order to deliver predicted molecule locations to a second microservice for analyzing number and location of predicted molecules. Similarly, the second microservice may execute analysis of predicted molecule locations to deliver immunotherapy response prediction according to an embodiment, above.

Where embodiments above are executed in one or more micro-services with or as part of a digital and laboratory health care platform, one or more of such micro-services may be part of an order management system that orchestrates the sequence of events as needed at the appropriate time and in the appropriate order necessary to instantiate embodiments above. A micro-services based order management system is disclosed, for example, in U.S. Patent Publication No. 2020/80365232, titled "Adaptive Order Fulfillment and Tracking Methods and Systems", and published Nov. 19, 2020, which is incorporated herein by reference and in its entirety for all purposes.

For example, continuing with the above first and second microservices, an order management system may notify the first microservice that an order for H&E image analysis and molecule location prediction has been received and is ready for processing. The first microservice may execute and notify the order management system once the delivery of predicted molecule locations is ready for the second microservice. Furthermore, the order management system may identify that execution parameters (prerequisites) for the second microservice are satisfied, including that the first microservice has completed, and notify the second microservice that it may continue processing the order to analyze predicted molecule locations and generate immunotherapy response prediction according to an embodiment, above.

Where the digital and laboratory health care platform further includes a genetic analyzer system, the genetic analyzer system may include targeted panels and/or sequencing probes. An example of a targeted panel is disclosed, for example, in U.S. Patent Publication No. 2021/0090694, titled "Data Based Cancer Research and Treatment Systems and Methods", and published Mar. 25, 2021, which is incorporated herein by reference and in its entirety for all purposes. An example of a targeted panel for sequencing cell-free (cf) DNA and determining various characteristics of a specimen based on the sequencing is disclosed, for example, in U.S. patent application Ser. No. 17/179,086, titled "Methods And Systems For Dynamic Variant Thresholding In A Liquid Biopsy Assay", and filed Feb. 18, 2021, U.S. patent application Ser. No. 17/179,267, titled "Estimation Of Circulating Tumor Fraction Using Off-Target Reads Of Targeted-Panel Sequencing", and filed Feb. 18, 2021, and U.S. patent application Ser. No. 17/179,279, titled "Methods And Systems For Refining Copy Number Variation In A Liquid Biopsy Assay", and filed Feb. 18, 2021 which is incorporated herein by reference and in its entirety for all purposes. In one example, targeted panels may enable the delivery of next generation sequencing results (including sequencing of DNA and/or RNA from solid or cell-free specimens) according to an embodiment, above. An example of the design of next-generation sequencing probes is disclosed, for example, in U.S. Patent Publication No. 2021/0115511, titled "Systems and Methods for Next Generation Sequencing Uniform Probe Design", and published Jun. 22, 2021 and U.S. patent application Ser. No. 17/323,986, titled "Systems and Methods for Next Generation Sequencing Uniform Probe Design", and filed May 18, 2021, which are incorporated herein by reference and in their entirety for all purposes.

Where the digital and laboratory health care platform further includes an epigenetic analyzer system, the epigenetic analyzer system may analyze specimens to determine their epigenetic characteristics and may further use that information for monitoring a patient over time. An example of an epigenetic analyzer system is disclosed, for example, in U.S. patent application Ser. No. 17/352,231, titled "Molecular Response And Progression Detection From Circulating Cell Free DNA", and filed Jun. 18, 2021, which is incorporated herein by reference and in its entirety for all purposes.

Where the digital and laboratory health care platform further includes a bioinformatics pipeline, the methods and systems described above may be utilized after completion or substantial completion of the systems and methods utilized in the bioinformatics pipeline. As one example, the bioinformatics pipeline may receive next-generation genetic sequencing results and return a set of binary files, such as one or more BAM files, reflecting DNA and/or RNA read counts aligned to a reference genome.

When the digital and laboratory health care platform further includes an RNA data normalizer, any RNA read counts may be normalized before processing embodiments as described above. An example of an RNA data normalizer is disclosed, for example, in U.S. Patent Publication No. 2020/0098448, titled "Methods of Normalizing and Correcting RNA Expression Data", and published Mar. 26, 2020, which is incorporated herein by reference and in its entirety for all purposes.

When the digital and laboratory health care platform further includes a genetic data deconvolver, any system and method for deconvolving may be utilized for analyzing genetic data associated with a specimen having two or more biological components to determine the contribution of each component to the genetic data and/or determine what genetic data would be associated with any component of the specimen if it were purified. An example of a genetic data deconvolver is disclosed, for example, in U.S. Patent Publication No. 2020/0210852, published Jul. 2, 2020, and PCT/US19/69161, filed Dec. 31, 2019, both titled "Transcriptome Deconvolution of Metastatic Tissue Samples"; and U.S. patent application Ser. No. 17/074,984, titled "Calculating Cell-type RNA Profiles for Diagnosis and Treatment", and filed Oct. 20, 2020, the contents of each of which are incorporated herein by reference and in their entirety for all purposes.

RNA expression levels may be adjusted to be expressed as a value relative to a reference expression level. Furthermore, multiple RNA expression data sets may be adjusted, prepared, and/or combined for analysis and may be adjusted to avoid artifacts caused when the data sets have differences because they have not been generated by using the same methods, equipment, and/or reagents. An example of RNA data set adjustment, preparation, and/or combination is disclosed, for example, in U.S. patent application Ser. No. 17/405,025, titled "Systems and Methods for Homogenization of Disparate Datasets", and filed Aug. 18, 2021.

When the digital and laboratory health care platform further includes an automated RNA expression caller, RNA expression levels associated with multiple samples may be compared to determine whether an artifact is causing anomalies in the data. An example of an automated RNA expression caller is disclosed, for example, in U.S. Pat. No. 11,043,283, titled "Systems and Methods for Automating RNA Expression Calls in a Cancer Prediction Pipeline", and issued Jun. 22, 2021, which is incorporated herein by reference and in its entirety for all purposes.

The digital and laboratory health care platform may further include one or more insight engines to deliver information, characteristics, or determinations related to a disease state that may be based on genetic and/or clinical data associated with a patient, specimen and/or organoid. Exemplary insight engines may include a tumor of unknown origin (tumor origin) engine, a human leukocyte antigen (HLA) loss of homozygosity (LOH) engine, a tumor mutational burden engine, a PD-L1 status engine, a homologous recombination deficiency engine, a cellular pathway activation report engine, an immune infiltration engine, a microsatellite instability engine, a pathogen infection status engine, a T cell receptor or B cell receptor profiling engine, a line of therapy engine, a metastatic prediction engine, an IO progression risk prediction engine, and so forth.

An example tumor origin or tumor of unknown origin engine is disclosed, for example, in U.S. patent application Ser. No. 15/930,234, titled "Systems and Methods for Multi-Label Cancer Classification", and filed May 12, 2020, which is incorporated herein by reference and in its entirety for all purposes.

An example of an HLA LOH engine is disclosed, for example, in U.S. Pat. No. 11,081,210, titled "Detection of Human Leukocyte Antigen Class I Loss of Heterozygosity in Solid Tumor Types by NGS DNA Sequencing", and issued Aug. 3, 2021, which is incorporated herein by reference and in its entirety for all purposes. An additional example of an HLA LOH engine is disclosed, for example, in U.S. patent application Ser. No. 17/304,940, titled "Detection of Human Leukocyte Antigen Loss of Heterozygosity", and filed Jun. 28, 2021, which is incorporated herein by reference and in its entirety for all purposes.

An example of a tumor mutational burden (TMB) engine is disclosed, for example, in U.S. Patent Publication No. 2020/0258601, titled "Targeted-Panel Tumor Mutational Burden Calculation Systems and Methods", and published Aug. 13, 2020, which is incorporated herein by reference and in its entirety for all purposes.

An example of a PD-L1 status engine is disclosed, for example, in U.S. Patent Publication No. 2020/0395097, titled "A Pan-Cancer Model to Predict The PD-L1 Status of a Cancer Cell Sample Using RNA Expression Data and Other Patient Data", and published Dec. 17, 2020, which is incorporated herein by reference and in its entirety for all purposes. An additional example of a PD-L1 status engine is disclosed, for example, in U.S. Pat. No. 10,957,041, titled "Determining Biomarkers from Histopathology Slide Images", issued Mar. 23, 2021, which is incorporated herein by reference and in its entirety for all purposes.

An example of a homologous recombination deficiency engine is disclosed, for example, in U.S. Pat. No. 10,975,445, titled "An Integrative Machine-Learning Framework to Predict Homologous Recombination Deficiency", and issued Apr. 13, 2021, which is incorporated herein by reference and in its entirety for all purposes. An additional example of a homologous recombination deficiency engine is disclosed, for example, in U.S. patent application Ser. No. 17/492,518, titled "Systems and Methods for Predicting Homologous Recombination Deficiency Status of a Specimen", filed Oct. 1, 2021, which is incorporated herein by reference and in its entirety for all purposes.

An example of a cellular pathway activation report engine is disclosed, for example, in U.S. Patent Publication No. 2021/0057042, titled "Systems And Methods For Detecting Cellular Pathway Dysregulation In Cancer Specimens", and published Feb. 25, 2021, which is incorporated herein by reference and in its entirety for all purposes.

An example of an immune infiltration engine is disclosed, for example, in U.S. Patent Publication No. 2020/0075169, titled "A Multi-Modal Approach to Predicting Immune Infiltration Based on Integrated RNA Expression and Imaging Features", and published Mar. 5, 2020, which is incorporated herein by reference and in its entirety for all purposes.

An example of an MSI engine is disclosed, for example, in U.S. Patent Publication No. 2020/0118644, titled "Microsatellite Instability Determination System and Related Methods", and published Apr. 16, 2020, which is incorporated herein by reference and in its entirety for all purposes. An additional example of an MSI engine is disclosed, for example, in U.S. Patent Publication No. 2021/0098078, titled "Systems and Methods for Detecting Microsatellite Instability of a Cancer Using a Liquid Biopsy", and published Apr. 1, 2021, which is incorporated herein by reference and in its entirety for all purposes.

An example of a pathogen infection status engine is disclosed, for example, in U.S. Pat. No. 11,043,304, titled "Systems And Methods For Using Sequencing Data For Pathogen Detection", and issued Jun. 22, 2021, which is incorporated herein by reference and in its entirety for all purposes. Another example of a pathogen infection status engine is disclosed, for example, in PCT/US21/18619, titled "Systems And Methods For Detecting Viral DNA From Sequencing", and filed Feb. 18, 2021, which is incorporated herein by reference and in its entirety for all purposes.

An example of a T cell receptor or B cell receptor profiling engine is disclosed, for example, in U.S. patent application Ser. No. 17/302,030, titled "TCR/BCR Profiling Using Enrichment with Pools of Capture Probes", and filed Apr. 21, 2021, which is incorporated herein by reference and in its entirety for all purposes.

An example of a line of therapy engine is disclosed, for example, in U.S. Patent Publication No. 2021/0057071, titled "Unsupervised Learning And Prediction Of Lines Of Therapy From High-Dimensional Longitudinal Medications Data", and published Feb. 25, 2021, which is incorporated herein by reference and in its entirety for all purposes.

An example of a metastatic prediction engine is disclosed, for example, in U.S. Pat. No. 11,145,416, titled "Predicting likelihood and site of metastasis from patient records", and issued Oct. 12, 2021, which is incorporated herein by reference and in its entirety for all purposes.

An example of an IO progression risk prediction engine is disclosed, for example, in U.S. patent application Ser. No. 17/455,876, titled "Determination of Cytotoxic Gene Signature and Associated Systems and Methods For Response Prediction and Treatment", and filed Nov. 19, 2021, which is incorporated herein by reference and in its entirety for all purposes.

An additional example of a microsatellite instability engine is disclosed, for example, in U.S. patent application Ser. No. 16/412,362, titled "A Generalizable and Interpretable Deep Learning Framework for Predicting MSI From Histopathology Slide Images", and filed May 4, 2019, which is incorporated herein by reference and in its entirety for all purposes.

An example of a radiomics engine is disclosed, for example, in U.S. patent application Ser. No. 16/460,975, titled "3D Radiomic Platform for Imaging Biomarker Development", and filed Jul. 2, 2019, which is incorporated herein by reference and in its entirety for all purposes.

An example of a tissue segmentation engine is disclosed, for example, in U.S. patent application Ser. No. 16/732,242, titled "Artificial Intelligence Segmentation Of Tissue Images", and filed Dec. 31, 2019, which is incorporated herein by reference and in its entirety for all purposes.

When the digital and laboratory health care platform further includes a report generation engine, the methods and systems described above may be utilized to create a summary report of a patient's genetic profile and the results of one or more insight engines for presentation to a physician. For instance, the report may provide to the physician information about the extent to which the specimen that was sequenced contained tumor or normal tissue from a first organ, a second organ, a third organ, and so forth. For example, the report may provide a genetic profile for each of the tissue types, tumors, or organs in the specimen. The genetic profile may represent genetic sequences present in the tissue type, tumor, or organ and may include variants, expression levels, information about gene products, or other information that could be derived from genetic analysis of a tissue, tumor, or organ.

The report may include therapies and/or clinical trials matched based on a portion or all of the genetic profile or insight engine findings and summaries. For example, the clinical trials may be matched according to the systems and methods disclosed in U.S. Patent Publication No. 2020/0381087, titled "Systems and Methods of Clinical Trial Evaluation", published Dec. 3, 2020, which is incorporated herein by reference and in its entirety for all purposes.

The report may include a comparison of the results (for example, molecular and/or clinical patient data) to a database of results from many specimens. An example of methods and systems for comparing results to a database of results are disclosed in U.S. Patent Publication No. 2020/0135303 titled "User Interface, System, And Method For Cohort Analysis" and published Apr. 30, 2020, and U.S. Patent Publication No. 2020/0211716 titled "A Method and Process for Predicting and Analyzing Patient Cohort Response, Progression and Survival", and published Jul. 2, 2020, which is incorporated herein by reference and in its entirety for all purposes. The information may be used, sometimes in conjunction with similar information from additional specimens and/or clinical response information, to match therapies likely to be successful in treating a patient, discover biomarkers or design a clinical trial.

Any data generated by the systems and methods and/or the digital and laboratory health care platform may be downloaded by the user. In one example, the data may be downloaded as a CSV file comprising clinical and/or molecular data associated with tests, data structuring, and/or other services ordered by the user. In various embodiments, this may be accomplished by aggregating clinical data in a system backend, and making it available via a portal. This data may include not only variants and RNA expression data, but also data associated with immunotherapy markers such as MSI and TMB, as well as RNA fusions.

When the digital and laboratory health care platform further includes a device comprising a microphone and speaker for receiving audible queries or instructions from a user and delivering answers or other information, the methods and systems described above may be utilized to add data to a database the device can access. An example of such a device is disclosed, for example, in U.S. Patent Publication No. 2020/0335102, titled "Collaborative Artificial Intelligence Method And System", and published Oct. 22, 2020, which is incorporated herein by reference and in its entirety for all purposes.

When the digital and laboratory health care platform further includes a mobile application for ingesting patient records, including genomic sequencing records and/or results even if they were not generated by the same digital and laboratory health care platform, the methods and systems described above may be utilized to receive ingested patient records. An example of such a mobile application is disclosed, for example, in U.S. Pat. No. 10,395,772, titled "Mobile Supplementation, Extraction, And Analysis Of Health Records", and issued Aug. 27, 2019, which is incorporated herein by reference and in its entirety for all purposes. Another example of such a mobile application is disclosed, for example, in U.S. Pat. No. 10,902,952, titled "Mobile Supplementation, Extraction, And Analysis Of Health Records", and issued Jan. 26, 2021, which is incorporated herein by reference and in its entirety for all purposes. Another example of such a mobile application is disclosed, for example, in U.S. Patent Publication No. 2021/0151192, titled "Mobile Supplementation, Extraction, And Analysis Of Health Records", and filed May 20, 2021, which is incorporated herein by reference and in its entirety for all purposes.

When the digital and laboratory health care platform further includes organoids developed in connection with the platform (for example, from the patient specimen), the methods and systems may be used to further evaluate genetic sequencing data derived from an organoid and/or the organoid sensitivity, especially to therapies matched based on a portion or all of the information determined by the systems and methods, including predicted cancer type(s), likely tumor origin(s), etc. These therapies may be tested on the organoid, derivatives of that organoid, and/or similar organoids to determine an organoid's sensitivity to those therapies. Any of the results may be included in a report. If the organoid is associated with a patient specimen, any of the results may be included in a report associated with that patient and/or delivered to the patient or patient's physician or clinician. In various examples, organoids may be cultured and tested according to the systems and methods disclosed in U.S. Patent Publication No. 2021/0155989, titled "Tumor Organoid Culture Compositions, Systems, and Methods", published May 27, 2021; PCT/US20/56930, titled "Systems and Methods for Predicting Therapeutic Sensitivity", filed Oct. 22, 2020; U.S. Patent Publication No. 2021/0172931, titled "Large Scale Organoid Analysis", published Jun. 10, 2021; PCT/US2020/063619, titled "Systems and Methods for High Throughput Drug Screening", filed Dec. 7, 2020 and U.S. patent application Ser. No. 17/301,975, titled "Artificial Fluorescent Image Systems and Methods", filed Apr. 20, 2021 which are each incorporated herein by reference and in their entirety for all purposes. In one example, the drug sensitivity assays may be especially informative if the systems and methods return results that match with a variety of therapies, or multiple results (for example, multiple equally or similarly likely cancer types or tumor origins), each matching with at least one therapy.

When the digital and laboratory health care platform further includes application of one or more of the above in combination with or as part of a medical device or a laboratory developed test that is generally targeted to medical care and research, such laboratory developed test or medical device results may be enhanced and personalized through the use of artificial intelligence. An example of laboratory developed tests, especially those that may be enhanced by artificial intelligence, is disclosed, for example, in U.S. Patent Publication No. 2021/0118559, titled "Artificial Intelligence Assisted Precision Medicine Enhancements to Standardized Laboratory Diagnostic Testing", and published Apr. 22, 2021, which is incorporated herein by reference and in its entirety for all purposes.

It should be understood that the examples given above are illustrative and do not limit the uses of the systems and methods described herein in combination with a digital and laboratory health care platform.

Additional Aspects

Aspect 1: A method for using a machine learning model to analyze at least one hematoxylin and eosin (H&E) slide image, the method comprising: a. receiving, at one or more processors, the H&E slide image; b. using, at the one or more processors, a machine learning model to predict locations of molecules in the H&E slide image, where the machine learning model is trained using a training data set comprising a plurality of unmarked H&E images and a plurality of marked H&E images, each marked H&E image being associated with one unmarked H&E image and each marked H&E image including a location of one or more molecules determined by analyzing a multiplex IHC image having at least two IHC stains, wherein each IHC stain has a unique color and a unique target molecule and wherein analyzing the multiplex IHC image includes determining an IHC stain that contributes to any two or more overlapping or adjacent IHC stains and comparing each IHC stain in the multiplex IHC image to a threshold; c. analyzing the number of predicted molecules and locations of the predicted molecules; and d. assigning an immunotherapy response class to the H&E slide image, based on the number of predicted molecules and/or locations of the predicted molecules.

Aspect 2: The method of Aspect 1 where the molecules are immunotherapy biomarkers selected from the group consisting of CD3, CD8, CD20, CD68, CK, PD1, and PDL1.

Aspect 3: The method of Aspect 1, further comprising locating individual cells.

Aspect 4: The method of Aspect 3, further comprising inferring, using the machine learning model, cell types for at least one of the individual cells.

Aspect 5: The method of Aspect 4, further comprising: predicting an immunotherapy response of the patient based, at least partially, on the inferred cell types.

Aspect 6: The method of Aspect 3, further comprising, for each individual cell associated with two or more classes of stained molecules, calculating the proportions of each stained molecule associated with the individual cell.

Aspect 7: The method of Aspect 6, further comprising: predicting an immunotherapy response of the patient based, at least partially, on the calculated proportions of each stained molecule associated with each individual cell.

Aspect 8: The method of Aspect 1, further comprising calculating a multifaceted score based on imaging features and genetic features.

Aspect 9: The method of Aspect 1, further comprising calculating additional statistics from the number of predicted molecules and locations of the predicted molecules.

Aspect 10: The method of Aspect 9, where the additional statistics include at least one of: percentage of cells having a particular molecule, percentage of cells having a particular ratio of molecules, location relationships among cell types, extent of mixing of cell types, and degree of tumor infiltration by lymphocytes.

Aspect 11: The method of Aspect 10, further comprising: predicting an immunotherapy response of the patient based, at least partially, on the additional statistics.

Aspect 12: The method of Aspect 1, wherein the assigning the immunotherapy response class includes comparing the number of predicted molecules to a threshold for each molecule.

Aspect 13: The method of Aspect 1, where the assigning the immunotherapy response class includes comparing locations of predicted molecules to molecule location criteria.

Aspect 14: The method of Aspect 1, where the immunotherapy response class is one of low, medium, and high lymphocyte infiltration.

Aspect 15: The method of Aspect 1, where the H&E image is associated with a patient.

Aspect 16: The method of Aspect 1, further comprising predicting an immunotherapy response of the patient, based on the number of predicted molecules and locations of the predicted molecules and matching with immunotherapy treatment.

Aspect 17: A method for using a machine learning model to analyze at least one H&E slide image associated with a patient, comprising: a. scoring H&E slide image for similarity to slide images associated with immunotherapy responders versus slide images associated with immunotherapy non-responders; and b. comparing the score to a threshold.

Aspect 18: The method of Aspect 17, where the H&E image is associated with a tumor organoid.

Aspect 19: The method of Aspect 18, which further includes the step of predicting an immunotherapy response of the tumor organoid, based on the number of predicted molecules and locations of the predicted molecules and predicting drug sensitivity response.

Aspect 20: A method for using a machine learning model to analyze at least one hematoxylin and eosin (H&E) slide image associated with a tumor organoid, the method comprising: a. scoring a H&E slide image for similarity to slide images associated with immunotherapy responders versus slide images associated with immunotherapy non-responders; and b. comparing the score of the H&E slide image to a threshold.

Aspect 21: A method for generating training data for a histology image-based machine learning model, the method comprising:
  a. obtaining at least one H&E slide image associated with a biological specimen;
  b. obtaining one or more multiplex immunohistochemistry (IHC) images associated with the biological specimen, wherein each multiplex IHC image includes at least two IHC stains, where each IHC stain has a unique color and a unique target molecule;
  c. for each multiplex IHC image, detecting mixture colors comprised of more than one IHC stain and identifying the IHC stains that comprise each mixture color;
  d. determining the location of each IHC stain color and determining the location of the associated stained target molecules;
  e. detecting individual cell locations and determining which individual cells are lymphocytes;
  f. for each H&E image and IHC image associated with the biological specimen, align/register images such that for each physical location in the biological specimen, all pixels associated with that physical location are aligned;
  g. for each target molecule, marking the location on the H&E image that corresponds to the locations of the target molecules stained on the IHC layers;
  h. for each cell having a location that corresponds to the location of one or more IHC stains, calculating the percentage of stained pixels overlapping the cell that is associated with each IHC stain to determine an IHC stain profile for each cell; and
  i. storing marked and unmarked versions of the H&E image as part of a training data set.

Aspect 22: The method of Aspect 21, where the H&E image is captured from a tissue layer that is stained only with H&E.

Aspect 23: The method of Aspect 21, where the H&E image is captured from a tissue layer that is stained with H&E and at least one IHC stain.

Aspect 24: The method of Aspect 21, where the H&E image is a virtual H&E stain image generated based on cell and tissue structures visible in a brightfield image of a tissue layer.

Aspect 25: The method of Aspect 21, where determining the location of each IHC stain color includes setting an intensity threshold for each stain color and comparing the intensity of the stain color in each pixel to the intensity threshold for that stain color.

Aspect 26: The method of Aspect 25, further comprising generating an overlay for each IHC stain where each pixel having an intensity that exceeds the threshold for the IHC stain is annotated to indicate presence of the IHC stain in the pixel.

Aspect 27: The method of Aspect 21, wherein detecting cell locations is performed by a neural network.

Aspect 28: The method of Aspect 21, where detecting cell locations includes the use of UNET.

Aspect 29: The method of Aspect 21, where identifying the IHC stains that comprise each mixture color is accomplished by deconvolving mixture colors within each image.

Aspect 30: The method of Aspect 21, further comprising assigning a tissue class to portions of the H&E image.

Aspect 31: The method of Aspect 21, further comprising associating an immunotherapy response score with the stored unmarked H&E image, based on clinical data associated with the biological specimen.

Aspect 32: The method of Aspect 31, where the immunotherapy response score is based on immunotherapy associated sequencing data, Immune Cell Infiltration, Immune Gene Expression Signatures, Multiplex PD-L1 and CD8 staining, and Multiplex macrophage IHC panels.

Aspect 33: The method of Aspect 31, where immunotherapy associated sequencing data includes tumor mutational burden (TMB), microsatellite Instability (MSI), and T Cell Clonality.

Aspect 34: The method of Aspect 21, repeating (a)-(i) for a plurality of biological specimens to generate the training data set.

Aspect 35: The method of Aspect 1, further comprising: e. receiving the biological specimen; f. dividing the biological specimen into a plurality of tissue layers; g. simultaneously adding at least two classes of antibody-conjugated (IHC) stain to one of the tissue layers, wherein each class of antibody-conjugated stain binds to a unique class of target molecule and each class of antibody-conjugated stain has a unique stain color, such that each stain color is associated with a target molecule; and h. for each of the stained layers, capturing and storing one digital image.

Aspect 36: The method of Aspect 35, wherein the target molecule in a first tissue layer is CD3; the target molecule in a second tissue layer is CD8; the target molecule in a third tissue layer is CD20; the target molecule in a fourth tissue layer is CD68; a fifth tissue layer is stained with H&E; the target molecules in a sixth tissue layer are CD3, CD8, CD20, CD68, CK, PD1, and PDL1; the target molecules in a seventh tissue layer are CD3, CD8, CD20, and CD68; the target molecules in an eighth tissue layer are CK, PD1, and PDL1; the target molecule in a ninth tissue layer is CK; the target molecule in a tenth tissue layer is PD1; and the target molecule in an eleventh tissue layer is PDL1.

Aspect 37: The method of Aspect 35, comprising simultaneously adding to one tissue layer of the tissue layers, a plurality of IHC stains such that the target molecules in the one tissue layer are CD3, CD8, CD20, CD68, CK, PD1, and PDL1.

Aspect 38: A method for training a histology image-based machine learning model, the method comprising: a. receiving a training data set comprising unmarked H&E images and data associated with each unmarked H&E image; and b. optimizing the histology image-based machine learning model to receive an unmarked H&E image and generate a simulated data set similar to the data associated with that unmarked H&E image.

Aspect 39: The method of Aspect 38, where the associated data includes a corresponding marked H&E image for each unmarked H&E image, wherein the marked H&E image shows the location of IHC staining target molecules in one or more IHC images associated with the same biological specimen as the H&E image, where at least one of the IHC images is a multiplex IHC image having two or more IHC stains.

Aspect 40: The method of Aspect 38, where the associated data includes an immunotherapy response score.

Aspect 41: The method of Aspect 38, wherein the training data set comprises a plurality of unmarked H&E images and a plurality of marked H&E images, each marked H&E image being associated with one unmarked H&E image and each marked H&E image including a location of one or more molecules determined by analyzing a multiplex IHC image having at least two IHC stains, wherein each IHC stain has a unique color and a unique target molecule and wherein analyzing the multiplex IHC image includes determining an IHC stain that contributes to any two or more overlapping or adjacent IHC stains and comparing each IHC stain in the multiplex IHC image to a threshold.

Aspect 42: The method of Aspect 38, further comprising receiving the training data set of Aspect 42.

Aspect 43: The method of Aspect 38, where the histology image-based machine learning model is a neural network.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components or multiple components.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a microcontroller, field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connects the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of the example methods described herein can be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method can be performed by one or more processors or processor-implemented hardware modules. The performance of certain of the operations may be distributed among the one or more processors, not only residing within a single machine, but also deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but also deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as an example only and does not describe every possible embodiment, as describing every possible embodiment would be impractical, if not impossible. One could implement numerous alternate embodiments, using either current technology or technology developed after the filing date of this application.

What is claimed is:

1. A method for using a machine learning model to analyze at least one hematoxylin and eosin (H&E) slide image, the method comprising:
   a. receiving, at one or more processors, the H&E slide image and providing the H&E slide image to a machine learning model;
   b. predicting, at the one or more processors, locations of molecules in the H&E slide image using the machine learning model where the machine learning model is trained using a training data set comprising a plurality of unmarked H&E images and a plurality of marked H&E images, each marked H&E image being associated with one unmarked H&E image and each marked H&E image including a location of one or more molecules determined by analyzing a multiplex IHC image having at least two IHC stains, wherein each IHC stain has a unique color and a unique target molecule and wherein analyzing the multiplex IHC image includes determining an IHC stain that contributes to any two or more overlapping or adjacent IHC stains and comparing each IHC stain in the multiplex IHC image to a threshold;
   c. analyzing the number of predicted molecules and locations of the predicted molecules predicted by the machine learning model; and
   d. assigning an immunotherapy response class to the H&E slide image, based on the number of predicted molecules and/or locations of the predicted molecules.

2. The method of claim 1 where the molecules are immunotherapy biomarkers selected from the group consisting of CD3, CD8, CD20, CD68, CK, PD1, and PDL1.

3. The method of claim 1, further comprising locating individual cells in the H&E slide image.

4. The method of claim 3, further comprising inferring, using the machine learning model, cell types for at least one of the individual cells.

5. The method of claim 4, further comprising: predicting an immunotherapy response of a patient based, at least partially, on the inferred cell types.

6. The method of claim 3, further comprising, for each individual cell associating the individual cell with one or more classes of stained molecules and for each individual cell associated with two or more classes of stained molecules, calculating the proportions of each stained molecule associated with the individual cell.

7. The method of claim 6, further comprising: predicting an immunotherapy response of a patient based, at least partially, on the calculated proportions of each stained molecule associated with each individual cell.

8. The method of claim 1, further comprising calculating a multifaceted score based on imaging features of the H&E slide image of a patient and genetic features of genetic data associated with the patient.

9. The method of claim 1, further comprising calculating statistics from the number of predicted molecules and locations of the predicted molecules.

10. The method of claim 9, where the statistics include at least one of: percentage of cells having a particular molecule, percentage of cells having a particular ratio of molecules, location relationships among cell types, extent of mixing of cell types, and degree of tumor infiltration by lymphocytes.

11. The method of claim 10, further comprising: predicting an immunotherapy response of a patient based, at least partially, on the additional statistics.

12. The method of claim 1, wherein the assigning the immunotherapy response class includes comparing the number of predicted molecules to a threshold for each molecule.

13. The method of claim 1, where the assigning the immunotherapy response class includes comparing locations of predicted molecules to molecule location criteria.

14. The method of claim 1, where the immunotherapy response class is one of low, medium, and high lymphocyte infiltration.

15. The method of claim 1, where the H&E image is associated with a patient.

16. The method of claim 1, further comprising predicting an immunotherapy response of a patient, based on the number of predicted molecules and locations of the predicted molecules and matching the number of predicted molecules and locations of the predicted molecules with an immunotherapy treatment.

17. The method of claim 1, wherein analyzing the multiplex IHC image having at least two IHC stains further comprises:
  e. receiving a biological specimen;
  f. dividing the biological specimen into a plurality of tissue layers;
  g. simultaneously adding the at least two IHC stains to one of the tissue layers, wherein each IHC stain corresponds to a different class of antibody-conjugated (IHC) stain, each class of antibody-conjugated stain is bound to a unique class of target molecules and each class of antibody-conjugated stain has a unique stain color, such that each stain color is associated with a different target molecule; and
  h. for each of the stained layers, capturing and storing one digital image.

18. The method of claim 17, wherein the target molecule in a first tissue layer is CD3; the target molecule in a second tissue layer is CD8; the target molecule in a third tissue layer is CD20; the target molecule in a fourth tissue layer is CD68; a fifth tissue layer is stained with H&E; the target molecules in a sixth tissue layer are CD3, CD8, CD20, CD68, CK, PD1, and PDL1; the target molecules in a seventh tissue layer are CD3, CD8, CD20, and CD68; the target molecules in an eighth tissue layer are CK, PD1, and PDL1; the target molecule in a ninth tissue layer is CK; the target molecule in a tenth tissue layer is PD1; and the target molecule in an eleventh tissue layer is PDL1.

19. The method of claim 17, comprising simultaneously adding to one tissue layer of the tissue layers, a plurality of the IHC stains such that the target molecules in the one tissue layer are CD3, CD8, CD20, CD68, CK, PD1, and PDL1.

20. A computing system for using a machine learning model to analyze at least one hematoxylin and eosin (H&E) slide image, the computing system comprising:
  one or more processors; and
  one or more memories having stored thereon computer-executable instructions that, when executed, cause the computing system to:
  receive the H&E slide image and provide the H&E slide image to a machine learning model;
  predict locations of molecules in the H&E slide image using the machine learning model, where the machine learning model is trained using a training data set comprising a plurality of unmarked H&E images and a plurality of marked H&E images, each marked H&E image being associated with one unmarked H&E image and each marked H&E image including a location of one or more molecules determined by analyzing a multiplex IHC image having at least two IHC stains, wherein each IHC stain has a unique color and a unique target molecule and wherein analyzing the multiplex IHC image includes determining an IHC stain that contributes to any two or more overlapping or adjacent IHC stains and comparing each IHC stain in the multiplex IHC image to a threshold;
  analyze the number of predicted molecules and locations of the predicted molecules predicted by the machine learning model; and
  assign an immunotherapy response class to the H&E slide image, based on the number of predicted molecules and/or locations of the predicted molecules.

21. The computing system of claim 20, where the molecules are immunotherapy biomarkers selected from the group consisting of CD3, CD8, CD20, CD68, CK, PD1, and PDL1.

22. The computing system of claim 20, the one or more memories having stored thereon instructions that, when executed, cause the computing system to: locate individual cells in the H&E slide image.

23. The computing system of claim 22, the one or more memories having stored thereon instructions that, when executed, cause the computing system to:
  infer, using the machine learning model, cell types for at least one of the individual cells; and
  predict an immunotherapy response of a patient based, at least partially, on the inferred cell types.

24. The computing system of claim 22, the one or more memories having stored thereon instructions that, when executed, cause the computing system to:
  for each individual cell associating the individual cell with one or more classes of stained molecules and for each individual cell associated with two or more classes of stained molecules, calculate the proportions of each stained molecule associated with the individual cell; and
  predict an immunotherapy response of a patient based, at least partially, on the calculated proportions of each stained molecule associated with each individual cell.

25. The computing system of claim 20, the one or more memories having stored thereon instructions that, when executed, cause the computing system to: calculate a multifaceted score based on imaging features of the H&E slide image of a patient and genetic features of genetic data associated with the patient.

26. The computing system of claim 20, the one or more memories having stored thereon instructions that, when executed, cause the computing system to:
  calculate statistics from the number of predicted molecules and locations of the predicted molecules, the statistics include at least one of: percentage of cells having a particular molecule, percentage of cells having a particular ratio of molecules, location relationships among cell types, extent of mixing of cell types, and degree of tumor infiltration by lymphocytes; and
  predict an immunotherapy response of a patient based, at least partially, on the additional statistics.

27. The computing system of claim 20, wherein instructions that, when executed, cause the computing system to assign the immunotherapy response class include instructions that, when executed, cause the computing system to:
  compare the number of predicted molecules to a threshold for each molecule; or compare locations of predicted molecules to molecule location criteria.

28. The computing system of claim 20, where the immunotherapy response class is one of low, medium, and high lymphocyte infiltration.

29. The computing system of claim 20, the one or more memories having stored thereon instructions that, when executed, cause the computing system to: predict an immunotherapy response of a patient, based on the number of predicted molecules and locations of the predicted molecules and matching the number of predicted molecules and locations of the predicted molecules with an immunotherapy treatment.

30. A non-transitory computer-readable medium, having stored thereon computer-executable instructions that, when executed by one or more processors, cause a computer to:
  receive an H&E slide image and provide the H&E slide image to a machine learning model;
  predict locations of molecules in the H&E slide image using the machine learning model, where the machine learning model is trained using a training data set comprising a plurality of unmarked H&E images and a plurality of marked H&E images, each marked H&E image being associated with one unmarked H&E image and each marked H&E image including a location of one or more molecules determined by analyzing a multiplex IHC image having at least two IHC stains, wherein each IHC stain has a unique color and a unique target molecule and wherein analyzing the multiplex IHC image includes determining an IHC stain that contributes to any two or more overlapping or adjacent IHC stains and comparing each IHC stain in the multiplex IHC image to a threshold;

analyze the number of predicted molecules and locations of the predicted molecules predicted by the machine learning model; and assign an immunotherapy response class to the H&E slide image, based on the number of predicted molecules and/or locations of the predicted molecules.

* * * * *